United States Patent
Yoshida et al.

(10) Patent No.: US 11,572,551 B2
(45) Date of Patent: Feb. 7, 2023

(54) HYDROLASE AND METHOD FOR PRODUCING (1S,2S)-1-ALKOXYCARBONYL-2-VINYLCYCLOPROPANE CARBOXYLIC ACID USING SAME

(71) Applicant: API CORPORATION, Tokyo (JP)

(72) Inventors: Toyokazu Yoshida, Gifu (JP); Koichi Ishida, Gifu (JP); Ryoma Miyake, Tokyo (JP); Takanobu Iura, Tokyo (JP); Hiroshi Kawabata, Tokyo (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 17/043,339

(22) PCT Filed: Mar. 29, 2019

(86) PCT No.: PCT/JP2019/013926
§ 371 (c)(1),
(2) Date: Sep. 29, 2020

(87) PCT Pub. No.: WO2019/189724
PCT Pub. Date: Oct. 3, 2019

(65) Prior Publication Data
US 2021/0024905 A1    Jan. 28, 2021

(30) Foreign Application Priority Data
Mar. 30, 2018  (JP) .............................. JP2018-070188

(51) Int. Cl.
*C12N 9/18*     (2006.01)
*C12P 7/62*     (2022.01)
*C12P 41/00*    (2006.01)

(52) U.S. Cl.
CPC .................. *C12N 9/18* (2013.01); *C12P 7/62* (2013.01); *C12P 41/00* (2013.01); *C12Y 301/01* (2013.01)

(58) Field of Classification Search
CPC ..................................... C12N 9/18; C12P 7/62
See application file for complete search history.

(56) References Cited

U.S. PATENT DOCUMENTS

2013/0096339 A1   4/2013   Asuma et al.
2013/0130338 A1   5/2013   Kawabata et al.

FOREIGN PATENT DOCUMENTS

| EP | 2 796 562 | 10/2014 |
|---|---|---|
| JP | 5613660 | 10/2014 |
| JP | 5657560 | 1/2015 |
| WO | 2012/029819 | 3/2012 |

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Greenblum & Bernstein, P.L.C.

(57) ABSTRACT

The present invention provides a novel hydrolase that can industrially produce optically highly pure (1S,2S)-1-alkoxycarbonyl-2-vinylcyclopropane carboxylic acid with high efficiency at low costs, and a production method using the hydrolase.

12 Claims, 2 Drawing Sheets
Specification includes a Sequence Listing.

(56) References Cited

OTHER PUBLICATIONS

Extended European Search Report issued in EP Patent Application No. 19777561.2, dated Jan. 10, 2022.
Database UniProt [Online], UniParc, Database accession No. UPI000B9AD34C, Dec. 20, 2017, XP002804883.
Database UniProt [Online], UniParc, Database accession No. UPI00070AAE76, Nov. 13, 2015, XP002804886.
Database UniProt [Online], UniParc, Database accession No. UPI00020740DB, Jun. 28, 2011, XP002804893.
"Alpha/beta hydrolase {EC0:00003131 EMBL:OZC62876.1}", A0A259Y6X7, [online], UniProtKB, https://www.uniprot.org/uniprot/A0A259Y6X7.txt?version=3, Feb. 28, 2018.
"Alpha/beta hydrolase {EC0:00003131 EMBL:KQU47217.1}", A0A0Q6JV16, [online], UniProtKB, https://www.uniprot.org/uniprot/A0A0Q6JV16.txt?version=11, Feb. 28, 2018.
"Alpha/beta hydrolase [Pseudonocardia dioxanivorans]", WP_013673631, [online], National Center for Biotechnology Information, https://www.ncbi.nlm.nih.gov/protein/WP_013673631, May 18, 2013.
"Alpha/beta hydrolase [Microbacterium chocolatum]", WP_053548180, [online], National Center for Biotechnology Information, https://www.ncbi.nlm.nih.gov/protein/92489447?sat=47&satkey=7881781, Sep. 3, 2015.
Fliche et al., "Enantioselective Synthesis of (1R,2S) and (1S,2S) Dehydrocoronamic Acids," *Synth. Commun.* vol. 24, No. 20, pp. 2873-2876 (1994).
International Search Report issued in PCT/JP2019/013926, dated Jun. 18, 2019, along with an English-language translation.
Written Opinion of the International Search Authority issued in PCT/JP2019/013926, dated Jun. 18, 2019, along with an English-language translation.

\* cited by examiner

Fig. 3

```
No
 2 RsD32Est   ------------------------------------------------MNLPPGV
 4 PdEst      ------------------------------------------------MQLLPGV
 6 McEst      ------------------------------------------------MTLFDGI
 - RhEst1     ------------------------------------------------MSIREAV
 8 AFX20780   ------------------------------------------------------ME
24 pnbA3027-m26 MTHQIVTTQYGKVKGTTENGVHKWKGIPYAKPPVGQWRFKAPEPPEVWEDVLDATAYGSI No
 2 RsD32Est   RSVTTQTSRLRLHHLEAGPVD----------------GVPLVLVHGNLSSGRFY-EDVMPA
 4 PdEst      RSVVVPTDRLEVHLVEYGPEE----------------GVPVVMLHGNLSTGRFF-EHLFPG
 6 McEst      TSRIVDTDRLTVNILERAADDPQTP----------PDRTVVFVHGNVSSALFW-QEIMQD
 - RhEst1     SVDGTSIVYRVTGNSAG--------------------TPLVLLHGWAQSSQCWGEQVLAD
 8 AFX20780   KRSITLKNGEVYKYVEQGQGD----------------QVLLLIHGNFSSLHF-TPLLER
24 pnbA3027-m26 CPQPSDLLSDSYTELPRQSEDCLYVNVFAPDTPSKNLPVMVWIHGGAFYLGAGSEPLYDG No
 2 RsD32Est   LAKTYR----VIAPDMRG----------FGDSERVTL DATRG LADWADDIAALLEALDID
 4 PdEst      APQGYR----IIAPDMRC----------FGDTERLPL DATRG LADWADDVAALLRALRVE
 6 McEst      LPSDLR----AIAVDLRG----------FGGSEHAPV DATRG VRDFSDDLHATLEALDIP
 - RhEst1     LAADYR----LIAVDLRG----------HGYS-DAPESGYDDSANWAGDVAAVLAAEGVT
 8 AFX20780   LPKNIK----VIAPDLRG----------YGDS--SYYRRISSLNDFAEDVHMFMEAKEIK
24 pnbA3027-m26 SKLAAQGEVIVVTLNYRLGPFGFLHLSSFNEAYSDNLGLLDQAAALKWVRENISAFGGDP No
 2 RsD32Est   QAPHLLGWS TGAGAITRYVLDGRTAAS---LTLMDPVP PYGF VGMHADGTPWFSDYAGCG
 4 PdEst      RPVHLLGWS T-AGAAIVDFASAHPVTS---LTFLDPVS PYGF GGVLADGTPCFPDFAGSG
 6 McEst      -VAHLVGWS MGGGVVMQYALD-HPVLS---LTLQSPVS PYGF GGTRRDGSRLTDDDAGCG
 - RhEst1     ENAILLGWS Y-GGLVICDYLAAHGTGA---VAGAVLVGAITSIGRGEKGGKVGSAMRSAV
 8 AFX20780   -SYHVVGWS LGGGVALELAAHHPEAVESLVLINSTTHKGYPVFKKGADGKPLVGEVYQSA
24 pnbA3027-m26 DNVTVFGES AGGMSIAALLAMPAAKGLFQKAIMESGASRTMTKEQAASTSAAFLQVLGIN No
 2 RsD32Est   AGVMNTEFTERIAAGDRSTDSLASPRNVAAGFWGEAPPIS--------QERVDVLIDELL
 4 PdEst      GGIVNPEVVRRLAEGDDTTESPFSIRSVMRGSYWLES-HS--------EPREDLLVAEVL
 6 McEst      GGGANPDFIQRLIDHDTSDDAQTSPRSVFR-AGYVASDYT--------TDHEDVWVESML
 - RhEst1     PGAMSEDPREAIRALGAFGNALTGPP------------------------
 8 AFX20780   DEMANDPVQVLPLLKAQKDKNFDFVSYIFDVTIYTVN-----------------------K
24 pnbA3027-m26 EGQLDKLHTVSAEDLLKAADQLRIAEKENQFQRFFQPALDPKTLPEEPEKAIAEGAASGI No
 2 RsD32Est   KTWVSEDNFPGSVVPSK NWPG IAPGTTGILNALSPKYCDWSRITELGSKPPIMWIQGGQD
 4 PdEst      KTVTGDDNYPGDSVASP NWPG SAPGTTGIINALSPKYCNWTRVVDLDPKPPVLWTHGAED
 6 McEst      TTSTADGNYPGDAVPSD NWPG FAAGRHGVLNTMAPQYFDVSGIVDLAEKPPILWIHGTAD
 - RhEst1     --------EGKGAASQALFGYSLSTRPRVRAALFNRAVGHDELLRNLDIPVLVLHGTDD
 8 AFX20780   PSVDDNKLWINESLKQRNLPDADWALANLNMSDQHNFYNAGMNNISKVKAPVLHTWGDKD
24 pnbA3027-m26 PLLIGTTRDEGYMFFTPDSDVHSQETLDAALEYLLGKPLAEKVADLYPRSLESQIHMMTD No
 2 RsD32Est   DVISNASHNDPATLGAAGLI PGWPG EDVCPAQPMITQIRDVLQAYEDAGGRTRTEWFEAS
 4 PdEst      TVVADASMQDLGTLGELGYV PGWPG ADVFPSQPMVSQIREVLGRYAAAGGHVRTEILPGA
 6 McEst      AIVSDASFYDLNYLGQLGIV PGWPG EDVAPAQEMVSQTRDVLGRYAAGGGTVTEVAVEGA
 - RhEst1     SVVDVSAGKHAEELIPKSQASYWVG-------------------------------C
 8 AFX20780   ITVPEYMIKDNVKALEEQSK-----------------------------LVVYENC
24 pnbA3027-m26 LLFWRPAVAYASAQSHYAPVWMYRFDWHPKKPPYNKAFHALELPFVFGNLDGLERMAKAE No
 2 RsD32Est   H H LPMIEEPDRWLQAVSSFVAEADAIA------------------------
 4 PdEst      G H SPHIELPELWSGVFWDFVGAAERG------------------------
 6 McEst      G H SAHLERPAVFRHALLEIIGYVGAAADPAPPTEAIIIRSAD---------
 - RhEst1     N H GPFVEDPTRFVSEVRTFISSLG-----------------------------
 8 AFX20780   G H SPLVDVPDQLTKDILDFIGYKG-----------------------------
24 pnbA3027-m26 ITDEVKQLSHTIQSAWITFAKTGNPSTEAVNWPAYHEETRETLILDSEITIENDPESEKR No
 2 RsD32Est   ----------
 4 PdEst      ----------
 6 McEst      ----------
 - RhEst1     ----------
 8 AFX20780   ----------
24 pnbA3027-m26 QKLFPSKGE
```

[----] Catalytic residues necessary for hydrolysis

[ ] Conserved motifs in hydrolases of SEQ ID NOs: 2, 4, and 6 only of the present invention

HYDROLASE AND METHOD FOR PRODUCING (1S,2S)-1-ALKOXYCARBONYL-2-VINYLCYCLOPROPANE CARBOXYLIC ACID USING SAME

TECHNICAL FIELD

The present invention relates to a novel hydrolase (esterase) that can be used for the production of (1S,2S)-1-alkoxycarbonyl-2-vinylcyclopropane carboxylic acid and use thereof.

BACKGROUND ART (1S,2S)-1-alkoxycarbonyl-2-vinylcyclopropane carboxylic acid is an intermediate useful for the production of various HCV NS3 protease inhibitors under development as a therapeutic drug for hepatitis C and the like.

Non-patent document 1, patent document 1 and patent document 2 describe a method for obtaining (1S,2S)-1-methoxycarbonyl-2-vinylcyclopropane carboxylic acid by hydrolyzing dimethyl 2-vinylcyclopropane-1,1-dicarboxylic acid by an enzyme.

However, the enzyme used in non-patent document 1 has insufficient optical selectivity, and the obtained (1S,2S)-1-methoxycarbonyl-2-vinylcyclopropane carboxylic acid has insufficient optical purity of 90% e.e., and thus the enzyme is not suitable for an industrial production method of an intermediate for a pharmaceutical product. The enzymes used in patent document 1 and patent document 2 have insufficient optical selectivity, a by-product (1S,2R)-1-methoxycarbonyl-2-vinylcyclopropane carboxylic acid is produced in a large amount besides the desired (1S,2S)-1-methoxycarbonyl-2-vinylcyclopropane carboxylic acid, which renders highly efficient production of the target product difficult to achieve. For industrial production, large separation device and large purification device are required, which increases the cost.

Therefore, a method for industrially producing (1S,2S)-1-alkoxycarbonyl-2-vinylcyclopropane carboxylic acid with high purity and high efficiency at low costs which is useful as an intermediate for the production of a therapeutic drug for hepatitis C and the like has been desired.

DOCUMENT LIST

Patent Documents patent document 1: JP-B-5613660
patent document 2: JP-B-5657560

Non-Patent Document non-patent document 1: C. Fliche et al. Synth. Commun. 24(20), 2873-2876 (1994)

SUMMARY OF INVENTION

Technical Problem

The problem to be solved by the present invention is provision of a novel hydrolase (esterase) for producing (1S,2S)-1-alkoxycarbonyl-2-vinylcyclopropane carboxylic acid with high optical purity and high selectivity. Furthermore, the problem to be solved by the present invention is provision of a novel method for industrially producing optically highly pure (1S,2S)-1-alkoxycarbonyl-2-vinylcyclopropane carboxylic acid with high efficiency at low costs.

Solution to Problem

The present inventors have conducted intensive studies in an attempt to solve the aforementioned problems and found that enzymes derived from *Rhodococcus* sp. D32 strain, *Pseudonocardia dioxanivorans* CB1190 strain, and *Microbacterium chocolatum* hydrolyze dialkyl 2-vinylcyclopropane-1,1-dicarboxylic acid with high selectivity and can afford (1S,2S)-1-alkoxycarbonyl-2-vinylcyclopropane carboxylic acid with high efficiency. They have also found that (1S,2S)-1-alkoxycarbonyl-2-vinylcyclopropane carboxylic acid with high optical purity, high selectivity and high concentration can be obtained at low costs by bringing the enzyme, a microorganism or cell having an ability to produce the enzyme, a treated product of the microorganism or cell, and/or a culture solution containing the enzyme obtained by culturing the microorganism or cell (hereinafter these are sometimes collectively referred to as "enzyme, etc.") into contact with dialkyl 2-vinylcyclopropane-1,1-dicarboxylic acid. Furthermore, they have found that optically highly pure (1R,2S)-1-amino-1-alkoxycarbonyl-2-vinylcyclopropane can also be produced with high efficiency at low costs by using the thus-obtained (1S,2S)-1-alkoxycarbonyl-2-vinylcyclopropane carboxylic acid. The present invention was completed based on these findings.

That is, the present invention provides the following.

[1] A hydrolase comprising a polypeptide of any of the following (a)-(e):
(a) a polypeptide having the amino acid sequence shown in SEQ ID NO: 2
(b) a polypeptide having the amino acid sequence shown in SEQ ID NO: 4 or 6, and an activity to catalyze the reaction shown in the formula (1):

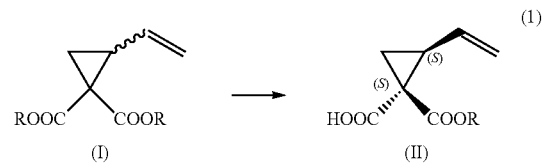

wherein R is an alkyl group having 1-6 carbon atoms
(c) a polypeptide having an amino acid sequence resulting from the deletion, insertion, substitution and/or addition of one or plural amino acids in the amino acid sequence shown in SEQ ID NO: 2, 4 or 6, and an activity to catalyze the reaction shown in the formula (1)
(d) a polypeptide having an amino acid sequence with not less than 60% of sequence identity with the amino acid sequence shown in SEQ ID NO: 2, 4 or 6, and an activity to catalyze the reaction shown in the above-mentioned formula (1)
(e) a polypeptide having an amino acid sequence with not less than 60% of sequence identity with the amino acid sequence shown in SEQ ID NO: 2, 4 or 6, wherein the aforementioned amino acid sequence comprises one or more motif sequences selected from the following motif sequences (i)-(iv)
(i) a sequence consisting of 5 consecutive residues (aspartic acid (D), alanine (A), threonine (T), arginine (R), glycine (G))

(ii) a sequence consisting of 4 consecutive residues (proline (P), tyrosine (Y), glycine (G), phenylalanine (F))
(iii) a sequence consisting of 4 consecutive residues (asparagine (N), tryptophan (W), proline (P), glycine (G))
(iv) a sequence consisting of 5 consecutive residues (proline (P), glycine (G), tryptophan (W), proline (P), glycine (G)).
[2] The hydrolase of [1], wherein R in the formula (1) is an ethyl group.
[3] A nucleic acid encoding hydrolase of [1] or [2].
[4] The nucleic acid of [3], wherein the aforementioned nucleic acid comprises a base sequence of the following (f), (g), (h) or (i):
(f) the base sequence shown in SEQ ID NO: 1, 3 or 5
(g) a nucleic acid having a base sequence resulting from the substitution, deletion, and/or addition of one or plural bases in the base sequence shown in SEQ ID NO: 1, 3 or 5, and encoding a polypeptide having an activity to catalyze the reaction shown in the formula (1)

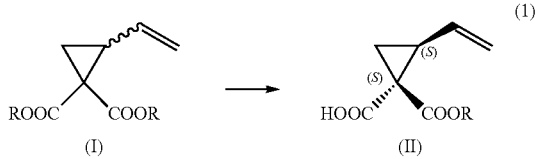

wherein R is an alkyl group having 1-6 carbon atoms
(h) a nucleic acid having a base sequence having not less than 60% of sequence identity with the base sequence shown in SEQ ID NO: 1, 3 or 5, and encoding a polypeptide having an activity to catalyze the reaction shown in the above-mentioned formula (1) (i) a nucleic acid having a base sequence that hybridizes with a complementary strand of the base sequence shown in SEQ ID NO: 1, 3 or 5 under stringent conditions, and encoding a polypeptide having an activity to catalyze the reaction shown in the above-mentioned formula (1).
[5] A method for producing (1S,2S)-1-alkoxycarbonyl-2-vinylcyclopropane carboxylic acid, comprising bringing the hydrolase of [1] or [2], a microorganism or cell having an ability to produce the aforementioned enzyme, a treated product of the aforementioned microorganism or cell, and/or a culture solution containing the aforementioned enzyme obtained by culturing the aforementioned microorganism or cell into contact with dialkyl 2-vinylcyclopropane-1,1-dicarboxylic acid represented by the formula (I) to produce (1S,2S)-1-alkoxycarbonyl-2-vinylcyclopropane carboxylic acid represented by the formula (II).
[6] The production method of [5], wherein the aforementioned microorganism or cell is a microorganism or cell transformed with the nucleic acid of [3] or [4].
[7] The recombinant vector comprising the nucleic acid of [3] or [4].
[8] A transformant comprising the recombinant vector of [7].

Advantageous Effects of Invention

According to the present invention, a novel hydrolase (esterase) for producing (1S,2S)-1-alkoxycarbonyl-2-vinylcyclopropane carboxylic acid which is useful as an intermediate for the production of a therapeutic drug for hepatitis C and the like can be provided with high optical purity and high selectivity. In addition, according to the present invention, a novel method for industrially producing optically highly pure (1S,2S)-1-alkoxycarbonyl-2-vinylcyclopropane carboxylic acid with high efficiency at low costs can be provided. Furthermore, optically highly pure (1R,2S)-1-amino-1-alkoxycarbonyl-2-vinylcyclopropane can be produced with high efficiency at low costs by using the thus-obtained (1S,2S)-1-alkoxycarbonyl-2-vinylcyclopropane carboxylic acid.

The (1S,2S)-1-alkoxycarbonyl-2-vinylcyclopropane carboxylic acid produced by the method of the present invention, and (1R,2S)-1-amino-1-alkoxycarbonyl-2-vinylcyclopropane produced using same can be utilized as a starting material or an intermediate for production in the production of a therapeutic drug for hepatitis C and the like.

BRIEF DESCRIPTION OF DRAWINGS

FIG. 3 shows the alignment of hydrolases.

DESCRIPTION OF EMBODIMENTS

Figure 1:
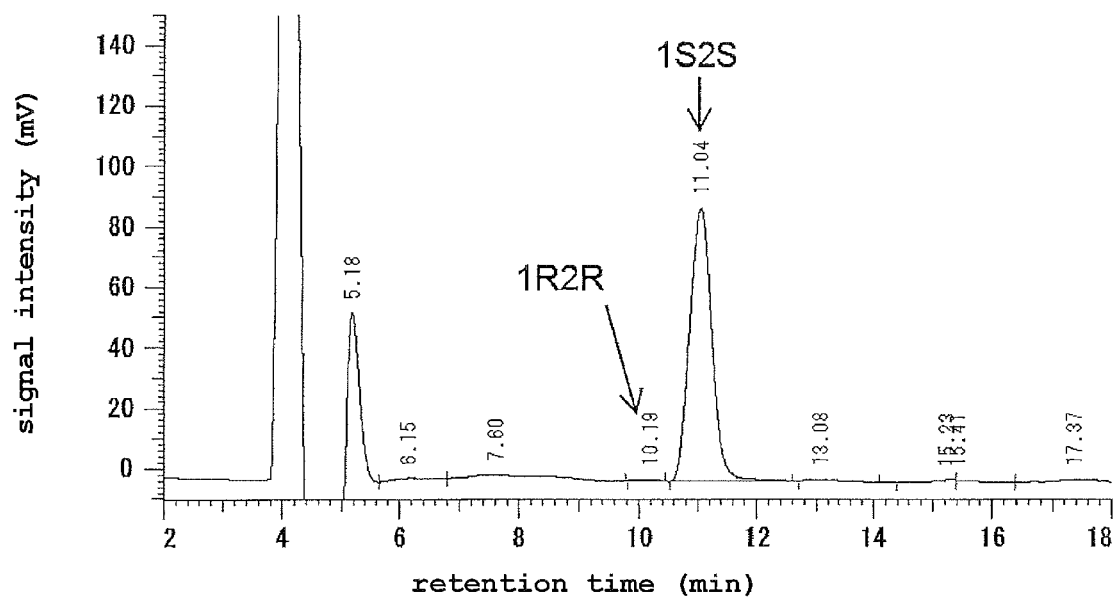
FIG. 1 shows HPLC analysis results of the reaction product obtained using a bacterium having the amino acid sequence D32Est in Example 1.

The present invention is explained in detail below.
1. Hydrolase of the Present Invention
The hydrolase of the present invention is one containing a polypeptide having the amino acid sequence shown in SEQ ID NO: 2, 4 or 6, or one containing a polypeptide having an amino acid sequence having high identity with the amino acid sequence (hereinafter sometimes to be referred to as "the homologue of the amino acid sequence") and having an activity to hydrolyze diethyl 2-vinylcyclopropane-1,1-dicarboxylic acid (hereinafter sometimes to be referred to as "the homologue of hydrolase"). Specifically, the novel hydrolase of the present invention contains a polypeptide of the following (a), (b), (c), (d) or (e):
(a) a polypeptide having the amino acid sequence shown in SEQ ID NO: 2
(b) a polypeptide having the amino acid sequence shown in SEQ ID NO: 4 or 6, and an activity to catalyze the reaction shown in the formula (1):

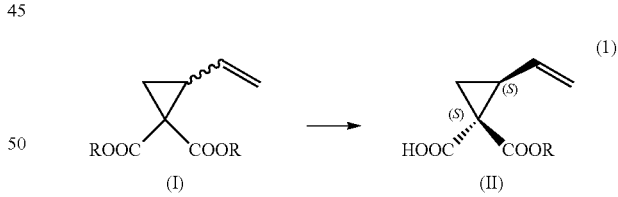

wherein R is an alkyl group having 1-6 carbon atoms
(c) a polypeptide having an amino acid sequence resulting from the deletion, insertion, substitution and/or addition of one or plural amino acids in the amino acid sequence shown in SEQ ID NO: 2, 4 or 6, and an activity to catalyze the reaction shown in the formula (1)
(d) a polypeptide having an amino acid sequence with not less than 60% of sequence identity with the amino acid sequence shown in SEQ ID NO: 2, 4 or 6, and an activity to catalyze the reaction shown in the above-mentioned formula (1)
(e) a polypeptide having an amino acid sequence with not less than 60% of sequence identity with the amino acid sequence shown in SEQ ID NO: 2, 4 or 6, wherein the aforementioned amino acid sequence comprises one or more motif sequences selected from the following motif sequences (i)-(iv)

(i) a sequence consisting of 5 consecutive residues (aspartic acid (D), alanine (A), threonine (T), arginine (R), glycine (G))

(ii) a sequence consisting of 4 consecutive residues (proline (P), tyrosine (Y), glycine (G), phenylalanine (F))

(iii) a sequence consisting of 4 consecutive residues (asparagine (N), tryptophan (W), proline (P), glycine (G))

(iv) a sequence consisting of 5 consecutive residues (proline (P), glycine (G), tryptophan (W), proline (P), glycine (G)).

In the formula (1), the alkyl group having 1-6 carbon atoms for R is, for example, a linear or branched alkyl group having 1-6 carbon atoms, more preferably a linear or branched alkyl group having 1-3 carbon atoms. Specific examples include methyl group, ethyl group, isopropyl group, normal propyl group, normal butyl group, isobutyl group, sec-butyl group, tert-butyl group, normal pentyl group, isopentyl group, tert-pentyl group, neopentyl group, normal hexyl group and the like. Among these, methyl group and ethyl group are preferable, and ethyl group is particularly preferable. In the formula (I), two Rs may be the same or different, preferably the same.

In the present invention, the homologue of a hydrolase with the amino acid sequence shown in SEQ ID NO: 2, 4 or 6 contains the polypeptide shown in the aforementioned (c), (d) or (e).

The polypeptide of the aforementioned (c) is a polypeptide having an amino acid sequence resulting from the deletion, insertion, substitution and/or addition of one or plural amino acids in the amino acid sequence shown in SEQ ID NO: 2, 4 or 6, and an activity to catalyze the reaction shown in the formula (1). In the case of substitution, one in which one or plural amino acids are conservatively substituted is preferable. In the present specification, that the "amino acids are conservatively substituted" means substitution of amino acids having similar chemical properties and the like and, for example, substitution of a basic amino acid with a basic amino acid and substitution of an acidic amino acid with an acidic amino acid can be mentioned.

The "one or plural amino acids" means generally 1-100, preferably 1-50, more preferably 1-20, further preferably 1-10, particularly preferably 1-5, amino acids.

The polypeptide of the aforementioned (d) is a polypeptide having an amino acid sequence with not less than 60% of sequence identity with the amino acid sequence shown in SEQ ID NO: 2, 4 or 6, and an activity to catalyze the reaction shown in the above-mentioned formula (1). Preferably, it is a polypeptide having an amino acid sequence with not less than 80%, more preferably not less than 90%, further preferably not less than 95%, of sequence identity with the full-length amino acid sequence shown in SEQ ID NO: 2, 4 or 6, and an activity to catalyze the reaction shown in the above-mentioned formula (1).

The homology (to be also referred to as identity or similarity) of the amino acid sequences in the present specification can be calculated using homology calculation algorithm NCBI BLAST (National Center for Biotechnology Information Basic Local Alignment Search Tool) and, for example, under the following conditions (expectancy=10; gap allowed; matrix=BLOSUM62; filtering-OFF). Examples of other algorithm for determining the homology of the amino acid sequence include the algorithm described in Karlin et al., Proc. Natl. Acad. Sci. USA, 90: 5873-5877 (1993) [said algorithm is incorporated in the NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [said algorithm is incorporated in the GAP program in the GCG software package], the algorithm described in Myers and Miller, CABIOS, 4: 11-17 (1988) [said algorithm is incorporated in ALIGN program (version2.0) which is a part of the CGC sequence alignment software package], the algorithm described in Pearson et al., Proc. Natl. Acad. Sci. USA, 85: 2444-2448 (1988) [said algorithm is incorporated in the FASTA program in the GCG software package] and the like, and these can also be similarly used preferably.

In the present invention, the activity to catalyze the reaction shown in the formula (1) is an activity to catalyze the reaction of hydrolyzing dialkyl 2-vinylcyclopropane-1,1-dicarboxylic acid represented by the formula (I) to produce (1S,2S)-1-alkoxycarbonyl-2-vinylcyclopropane carboxylic acid represented by the formula (II).

There are two kinds of stereoisomers ((2R) isomer and (2S) isomer) of dialkyl 2-vinylcyclopropane-1,1-dicarboxylic acid. Unless there are special conditions that cause inversion of configuration at the 2-position, (2S) isomer alone can be basically the starting material of the (1S,2S)-1-alkoxycarbonyl-2-vinylcyclopropane carboxylic acid of interest.

Therefore, the activity to catalyze the reaction shown in the formula (1) is an activity to catalyze the reaction with selectivity of preferentially hydrolyzing only the pro-R alkoxycarbonyl group from the two alkoxycarbonyl groups bonded to the prochiral carbon at the 1-position of dialkyl (2S)-2-vinylcyclopropane-1,1-dicarboxylic acid to preferentially produce (1S,2S)-1-alkoxycarbonyl-2-vinylcyclopropane carboxylic acid.

The pro-R is a notation that distinguishes between two Xs on $CX_2YZ$, and determines the priority order of respective substituents on C according to the CIP rule. Assuming that one of the two Xs has a higher priority order than the other, the relationship of the priority order with Y and Z is not changed. Based on the tentative priority order, whether the chirality of the central carbon is R or S is determined by the RS notation. In the case of R isomer, the priority X at that time is set as pro-R, and in the case of S isomer, it is set as pro-S.

This selectivity can be confirmed using the ratio of (1S,2S) isomer and (1R,2S) isomer of 1-alkoxycarbonyl-2-vinylcyclopropane carboxylic acid produced by hydrolysis as an index. The lower the amount of (1R,2S) isomer produced is compared to the amount of (1S,2S) isomer produced, the more improved is the yield of (1S,2S)-1-alkoxycarbonyl-2-vinylcyclopropane carboxylic acid, which is advantageous for industrialization.

The production ratio of the (1S,2S) isomer and the (1R,2S) isomer can be compared using the ratio of the Anti isomer produced and the Syn isomer produced as an index. The Anti isomer and Syn isomer refer to geometric isomers, the (1S,2S) isomer and the (1R,2R) isomer are Anti isomers, and the (1R,2S) isomer and the (1S,2R) isomer are Syn isomers. In the present invention, since the product resulting from hydrolysis is mainly composed of the (1S,2S) isomer, the resultant product can be quantified not only by the evaluation system for quantifying the (1S,2S) isomer alone, but also an evaluation system capable of separating an Anti isomer and a Syn isomer. That is, when the (1S,2S) isomer is quantified, it can be replaced by quantification of the amount of Anti isomer produced. Similarly, when the (1R,2S) isomer is quantified, it can be replaced by quantification of the amount of Syn isomer produced. The lower the ratio of Syn isomer produced is, the more improved is the yield of (1S,2S)-1-alkoxycarbonyl-2-vinylcyclopropane carboxylic acid, which is advantageous for industrialization.

These selectivities can be confirmed by contacting a racemate dialkyl 2-vinylcyclopropane-1,1-dicarboxylic acid with the hydrolase of interest and the like to produce 1-alkoxycarbonyl-2-vinylcyclopropane carboxylic acid, and measuring the amount of the (1S,2S) isomer and the (1R,2S) isomer of l-alkoxycarbonyl-2-vinylcyclopropane carboxylic acid produced, or by measuring the amount of the Anti isomer and the Syn isomer produced.

The contact method is not particularly limited and includes, for example, adding racemic dialkyl 2-vinylcyclopropane-1,1-dicarboxylic acid to a liquid containing the aforementioned hydrolase of interest, and reacting them at a suitable temperature (e.g., about 10° C.-45° C.) and pressure (e.g., about atmospheric pressure) and the like.

When the racemic dialkyl 2-vinylcyclopropane-1,1-dicarboxylic acid is hydrolyzed, hydrolysis of (2R) isomer results in the production of (1S,2R) isomer and (1R,2R) isomer. It is preferable to suppress the production amount of (1R,2R) isomer to a low level, which is the enantiomer of the (1S,2S) isomer of interest. Therefore, in the present invention, it is more preferable to have selectivity to preferentially produce (1S,2R)-1-alkoxycarbonyl-2-vinylcyclopropane carboxylic acid by preferentially hydrolyzing only a pro-R alkoxycarbonyl group from the two alkoxycarbonyl groups bonded to the prochiral carbon at the 1-position of dialkyl (2R)-2-vinylcyclopropane-1,1-dicarboxylic acid. Similarly, it is further preferable to have selectivity to preferentially hydrolyze dialkyl (2S)-2-vinylcyclopropane-1,1-dicarboxylic acid than dialkyl (2R)-2-vinylcyclopropane-1,1-dicarboxylic acid. The both selectivities can be measured by enantiomeric excess (% e.e.) of (1S,2S) isomer with respect to the (1R,2R) isomer of 1-alkoxycarbonyl-2-vinylcyclopropanecarboxylic acid produced by hydrolysis. The higher the enantiomeric excess of the (1S,2S) isomer, less likely it is that the subsequent production process and the physiological activity of the produced pharmaceutical product will be adversely affected, which is industrially advantageous.

The polypeptide of the aforementioned (e) is a polypeptide having an amino acid sequence with not less than 60% of sequence identity with the amino acid sequence shown in SEQ ID NO: 2, 4 or 6, wherein the amino acid sequence comprises one or more motif sequences selected from the following motif sequences (i)-(iv)
(i) a sequence consisting of 5 consecutive residues (aspartic acid (D), alanine (A), threonine (T), arginine (R), glycine (G))
(ii) a sequence consisting of 4 consecutive residues (proline (P), tyrosine (Y), glycine (G), phenylalanine (F))
(iii) a sequence consisting of 4 consecutive residues (asparagine (N), tryptophan (W), proline (P), glycine (G))
(iv) a sequence consisting of 5 consecutive residues (proline (P), glycine (G), tryptophan (W), proline (P), glycine (G)).

In the present invention, the motif sequence refers to a small structural portion found in the amino acid sequence of a polypeptide. It is known that a group of polypeptides (proteins) that retain a particular function have a common characteristic motif sequence. For example, it is known that serine (S), aspartic acid (D), and histidine (H) are amino acid residues necessary for catalytic activity (hydrolyzing function) in a particular kind of hydrolase. Specifically, the hydrolase RhEst1 shown in Catalysis Science and Technology, 2015, vol. 5, 2622 has serine (S), aspartic acid (D) and histidine (H) as amino acid residues. As shown in FIG. 3, the hydrolase AFX20780 described in U.S. Pat. No. 8,298,799 also has serine (S), aspartic acid (D) and histidine (H) as amino acid residues at particular positions.

As shown in FIG. 3, the amino acid sequence shown in SEQ ID NO: 2, 4 or 6 of the present invention also has serine (S), aspartic acid (D) and histidine (H) at particular positions, similar to the aforementioned hydrolase RhEst1 and AFX20780, and has catalytic activity (hydrolysis function).

As shown in FIG. 3, the amino acid sequence shown in SEQ ID NO: 2, 4 or 6 of the present invention has, as characteristic motif sequence(s), one or more motif sequences selected from the following motif sequences (i)-(iv)
(i) a sequence consisting of 5 consecutive residues (aspartic acid (D), alanine (A), threonine (T), arginine (R), glycine (G))
(ii) a sequence consisting of 4 consecutive residues (proline (P), tyrosine (Y), glycine (G), phenylalanine (F))
(iii) a sequence consisting of 4 consecutive residues (asparagine (N), tryptophan (W), proline (P), glycine (G))
(iv) a sequence consisting of 5 consecutive residues (proline (P), glycine (G), tryptophan (W), proline (P), glycine (G)).

These motif sequences are commonly possessed by the amino acid sequences shown in SEQ ID NO: 2, 4 and 6 of the present invention besides the aforementioned serine (S), aspartic acid (D) and histidine (H). It is thus presumed that they are motif sequences for stereoselectively hydrolyzing dialkyl 2-vinylcyclopropane-1,1-dicarboxylic acid, which is the characteristic function of the enzyme of the present invention having the amino acid sequence. These motif sequences may function independently, or a plurality of motif sequences may act simultaneously to exert the desired function.

As described above, the hydrolase of the present invention contains a polypeptide having the amino acid sequence shown in SEQ ID NO: 2, 4 or 6, or is a homologue of the amino acid sequence and containing a polypeptide having a hydrolytic activity on dialkyl 2-vinylcyclopropane-1,1-dicarboxylic acid. The level of the activity of the hydrolase containing a polypeptide having the homologue of the amino acid sequence to hydrolyze dialkyl 2-vinylcyclopropane-1,1-dicarboxylic acid may be quantitatively equivalent to that of a hydrolase containing a polypeptide having the amino acid sequence shown in SEQ ID NO: 2, 4 or 6, or may vary within an acceptable range (e.g., about 0.1-about 5 times, preferably about 0.3-about 3 times).

The amino acid sequences shown in SEQ ID NO: 2, 4 and 6 are each derived from *Rhodococcus* sp. D32 strain, *Pseudonocardia dioxanivorans* CB1190 strain and *Microbacterium chocolatum*. These amino acid sequences were identified by the present inventors to be hydrolases of dialkyl 2-vinylcyclopropane-1,1-dicarboxylic acid.

The polypeptide having the amino acid sequence shown in SEQ ID NO: 2 is a polypeptide derived from *Rhodococcus* sp. D32 strain, and the strain is a bacterium recovered from a soil sample. The amino acid sequence shown in SEQ ID NO: 2 was obtained by the analysis of the N-terminal sequence of dialkyl 2-vinylcyclopropane-1,1-dicarboxylic acid hydrolase produced by the bacterium and the analysis of the chromosomal DNA of *Rhodococcus* sp. D32 strain.

The polypeptides having the amino acid sequences shown in SEQ ID NO: 4 and 6 are sequences obtained from the genomic information of the microorganisms from which they are derived. The amino acid sequences shown in SEQ ID NO: 4 and 6 are respectively the same as GenBank accession Nos. WP-013673631 and WP-053548180 which are amino acid sequences encoded by a DNA sequence predicted to encode a protein. There are no reports that actually confirmed the existence of any of them, such as isolation as a protein. Naturally, their function as a protein was completely unknown.

In the present invention, a polypeptide having the amino acid sequence shown in SEQ ID NO: 2 is preferable since it shows high yield of (1S,2S)-1-alkoxycarbonyl-2-vinylcyclopropane carboxylic acid and high selectivity among the polypeptides having the amino acid sequences shown in SEQ ID NO: 2, 4 and 6.

The hydrolase containing a polypeptide having the amino acid sequence shown in SEQ ID NO: 2, 4 or 6 of the present invention can also be obtained from *Rhodococcus* sp. D32 strain, *Pseudonocardia dioxanivorans* CB1190 strain, or *Microbacterium chocolatum*, respectively, by purification and isolation by a known method. Examples of the purification method include solvent extraction, distillation, column chromatography, liquid chromatography, recrystallization, combination thereof and the like.

In addition, the hydrolase of the present invention can also be produced by culturing a transformant containing a nucleic acid encoding same, and separating and purifying the hydrolase from the obtained culture. The nucleic acid encoding the hydrolase of the present invention may be a DNA or an RNA, or DNA/RNA chimera. It is preferably a DNA. The nucleic acid may be double stranded or single stranded. When the nucleic acid is double stranded, it may be a double stranded DNA, a double stranded RNA or a DNA:RNA hybrid. When the nucleic acid is single stranded, it may be a sense strand (that is, coding strand) or antisense strand (that is, non-coding strand).

As the DNA encoding the hydrolase of the present invention, synthetic DNA or the like can be mentioned. For example, it can be obtained by converting full-length hydrolase cDNA which was directly amplified by Reverse Transcriptase-PCR using total RNA or mRNA fraction prepared from the cells or tissues derived from *Rhodococcus* sp. D32 strain, *Pseudonocardia dioxanivorans* CB1190 strain or *Microbacterium* chocolatum as a template, according to a method known per se such as ODA-LA PCR method, Gapped duplex method, Kunkel method and the like or a method analogous thereto, and using a known kit, for example, Mutan™-super Express Km (TAKARA BIO INC.), Mutan™-K (TAKARA BIO INC.) or the like. Alternatively, it can also be obtained from a cDNA library prepared by inserting the above-mentioned total RNA or mRNA fragments in suitable vectors, by converting, according to the above-mentioned method, the cDNA cloned by a colony or plaque hybridization method, PCR method or the like. The vector used for the library may be any such as bacteriophage, plasmid, cosmid, phagemid or the like.

Examples of the nucleic acid encoding the polypeptide having the amino acid sequence shown in SEQ ID NO: 2, 4 or 6 include nucleic acids containing the base sequence shown in SEQ ID NO: 1, 3 or 5, respectively. It may be a nucleic acid containing a base sequence having high identity with the base sequence of SEQ ID NO: 1, 3 or 5 (hereinafter sometimes to be referred to as "nucleic acid homologue") as long as it encodes a polypeptide having the activity to catalyze the reaction shown by the formula (1). That is, examples of the nucleic acid encoding the polypeptide include those having the base sequence shown in the following (f), (g), (h) or (i):
(f) a nucleic acid having the base sequence shown in SEQ ID NO: 1, 3 or 5
(g) a nucleic acid having a base sequence resulting from the substitution, deletion, and/or addition of one or plural bases in the base sequence shown in SEQ ID NO: 1, 3 or 5, and encoding a polypeptide having an activity to catalyze the reaction shown in the above-mentioned formula (1)
(h) a nucleic acid having a base sequence having not less than 60% of sequence identity with the base sequence shown in SEQ ID NO: 1, 3 or 5, and encoding a polypeptide having an activity to catalyze the reaction shown in the above-mentioned formula (1)
(i) a nucleic acid having a base sequence that hybridizes with a complementary strand of the base sequence shown in SEQ ID NO: 1, 3 or 5 under stringent conditions, and encoding a polypeptide having an activity to catalyze the reaction shown in the above-mentioned formula (1).

The homologue of the nucleic acid of the aforementioned (g) is, for example, a nucleic acid containing a base sequence resulting from deletion, substitution, insertion and/or addition of one or plural bases in the base sequence shown in SEQ ID NO: 1, 3 or 5 and encoding a polypeptide having an activity to catalyze the reaction shown in the above-mentioned formula (1). In the case of substitution, insertion or addition, one or plural bases are preferably substituted, inserted or added. As used herein, "one or plural bases" refers to, for example, 1-300, preferably 1-150, more preferably 1-60, further preferably 1-30, particularly preferably 1-15, bases.

The base sequence shown in SEQ ID NO: 1, 3 or 5 is a base sequence resulting from codon optimization of the gene of *Rhodococcus* sp. D32 strain-derived hydrolase RsD32Est (SEQ ID NO: 2), *Pseudonocardia dioxanivorans* CB1190 strain-derived hydrolase PdEst (SEQ ID NO: 4), or *Microbacterium chocolatum*-derived hydrolase McEst (SEQ ID NO: 6), respectively, for *Escherichia coli* expression. Such DNAs with codons optimized according to the host to be transformed are naturally encompassed in the nucleic acid encoding polypeptide having an activity to catalyze the reaction shown in the above-mentioned formula (1) and usable in the present invention.

The homologue of the nucleic acid of the aforementioned (h) is, for example, a nucleic acid having a base sequence with not less than 60% of sequence identity with the base sequence of SEQ ID NO: 1, 3 or 5, and encoding a polypeptide having an activity to catalyze the reaction shown in the above-mentioned formula (1). Preferably, it is a nucleic acid having a base sequence with a homology (also referred to as an identity) of not less than 80%, more preferably not less than 90%, further preferably not less than 95%, further more preferably not less than 98%, with the base sequence shown in SEQ ID NO: 1, 3 or 5, and encoding a polypeptide having an activity to catalyze the reaction shown in the above-mentioned formula (1).

The homology (to be also referred to as identity) of the base sequences in the present specification can be calculated using homology calculation algorithm NCBI BLAST (National Center for Biotechnology Information Basic Local Alignment Search Tool) and, for example, under the following conditions (expectancy=10; gap allowed; filtering=ON; matching score=1; mismatch score=−3). Similar preferable examples of other algorithm for determining the homology of the base sequence include the above-mentioned homology calculation algorithm of amino acid sequence.

The homologue of the nucleic acid of the aforementioned (h) may be a nucleic acid that hybridizes to the complementary strand of the base sequence of SEQ ID NO: 1, 3 or 5 under stringent conditions as long as it encodes a polypeptide having an activity to catalyze the reaction shown in the above-mentioned formula (1). The "stringent conditions" here can be appropriately determined by reference to the conditions in previous reports (e.g., Current Protocols in Molecular Biology, John Wiley & Sons, 6.3.16.3.6, 1999). Specifically, for example, the conditions include washing once, more preferably 2-3 times, at the salt concentration and temperature corresponding to the washing conditions of general Southern hybridization; 60° C., 1×SSC, 0.1% SDS, preferably, 0.1×SSC, 0.1% SDS, further preferably, 65° C., 0.1×SSC, 0.1% SDS, 68° C., 0.1×SSC, 0.1% SDS etc. (highly stringent conditions), and the like can be mentioned.

Those of ordinary skill in the art can appropriately carry out substitution, deletion, insertion and/or addition to the nucleic acid shown in SEQ ID NO: 1, 3 or 5 by using a site-specific mutagenesis method (Nucleic Acids Res. 10, pp. 6487 (1982), Methods in Enzymol. 100, pp. 448 (1983), Molecular Cloning, PCR A Practical Approach IRL Press pp. 200 (1991)) and the like to introduce the desired mutation, whereby a homologue of the above-mentioned nucleic acid can be obtained.

The nucleic acid of the present invention can encode a polypeptide having an activity to catalyze the reaction shown in the above-mentioned formula (1). When the nucleic acid of the present invention has a base sequence shown in SEQ ID NO: 1, 3 or 5, or a base sequence having high identity with the base sequence shown in SEQ ID NO: 1, 3 or 5, the level of the activity of the hydrolase containing a polypeptide encoded by the nucleic acid to hydrolyze dialkyl 2-vinylcyclopropane-1,1-dicarboxylic acid may be quantitatively equivalent to that of a hydrolase containing a polypeptide having the amino acid sequence shown in SEQ ID NO: 2, 4 or 6, or that containing a polypeptide having the homologue of the amino acid sequence, or may vary within an acceptable range (e.g., about 0.1-about 5 times, preferably about 0.3-about 3 times).

In addition, based on the amino acid sequence shown in SEQ ID NO: 2, 4 or 6 or a part thereof, the base sequence shown in SEQ ID NO: 1, 3 or 5 or a part thereof, it is also possible to perform homology search on, for example, a database such as DNA Databank of JAPAN (DDBJ) and the like to obtain the amino acid sequence information of the polypeptide having an activity to catalyze the reaction shown by the formula (1) or the base sequence information of the DNA encoding the same.

The hydrolase of the present invention has the activity to catalyze the reaction shown by the above-mentioned formula (1) with higher selectivity than the conventionally known hydrolase containing the polypeptide shown in SEQ ID NO: 24. In addition, the hydrolase of the present invention shows low production ratios of (1S,2R) isomer, (1R,2S) isomer and/or (1R,2R) isomer of 1-alkoxycarbonyl-2-vinyl-cyclopropane carboxylic acid when dialkyl 2-vinylcyclopropane-1,1-dicarboxylic acid is hydrolyzed. Particularly, the production ratios of the (1S,2R) isomer, (1R,2S) isomer and/or (1R,2R) isomer are lower than those of a hydrolase containing the polypeptide shown in SEQ ID NO: 24.

In the below-mentioned production method of the present invention, the aforementioned hydrolase may be directly used for the reaction with dialkyl 2-vinylcyclopropane-1,1-dicarboxylic acid; however, it is preferable to use a microorganism or cell capable of producing the enzyme, a treated product of the microorganism or cell, and/or a culture solution containing the enzyme obtained by culturing the microorganism or cell.

As the microorganism or cell having the ability to produce the hydrolase of the present invention, a microorganism or cell that originally has an ability to produce the hydrolase may be used, or a microorganism or cell imparted with the aforementioned producing ability by breeding may be used. The microorganism or cell may be alive or dead and, for example, a quiescent bacterium or the like can be preferably used. Examples of the species of the microorganism or the type of the cell having the ability to produce the hydrolase of the present invention include those described below as the "host microorganism" or "host cell".

As a means for imparting the aforementioned producing ability by breeding, known methods such as a gene recombination treatment (transformation), a mutation treatment and the like can be adopted. As a method of transformation, a method for introducing the DNA of interest, a method of enhancing the expression of a DNA of interest by modifying an expression regulatory sequence such as a promoter on a chromosome, and the like can be mentioned.

Among these, it is preferable to use a microorganism or cell transformed with DNA encoding the aforementioned polypeptide of the present invention.

A nucleic acid (DNA) encoding the polypeptide (hydrolase) of the present invention can be cloned by, as described above, PCR using chromosomal DNA derived from *Rhodococcus* sp. D32 strain, *Pseudonocardia dioxanivorans* CB1190 strain or *Microbacterium* chocolatum as a template, and appropriate primers.

A nucleic acid (DNA) encoding the polypeptide (hydrolase) of the present invention can be cloned by, as described above, preparing full-length hydrolase cDNA directly amplified by RT-PCR using total RNA or mRNA derived from *Rhodococcus* sp. D32 strain, *Pseudonocardia dioxanivorans* CB1190 strain or *Microbacterium chocolatum* as a template, followed by PCR using appropriate primers.

For example, by inserting the DNA encoding the polypeptide of the present invention obtained as mentioned above into a known expression vector in an expressible configuration, the polypeptide gene expression vector of the present invention is provided. Then, by transforming the host cell with the expression vector, a transformant into which a DNA encoding the polypeptide of the present invention is introduced can be obtained. The transformant can also be obtained by expressively incorporating the DNA encoding the polypeptide of the present invention into the chromosomal DNA of the host by a method such as homologous recombination and the like.

In the present specification, the "expression vector" is a genetic element incorporating a polynucleotide encoding a protein having a desired function used for replicating and expressing a protein having a desired function in the aforementioned host organism, by introduction into a host organism. Examples thereof include, but are not limited to, plasmid, virus, phage, cosmid and the like. Preferable expression vector is a plasmid.

In the present specification, the "transformant" means a microorganism or cell into which the gene of interest is introduced using the aforementioned expression vector and the like, and which has acquired an ability to show a desired phenotype associated with a protein having a desired function. Specifically, as a method for producing a transformant, a method including introducing a DNA encoding the polypeptide of the present invention into a plasmid vector, a phage vector, or a viral vector that is stably present in a host cell, and introducing the constructed expression vector into the host cell, and a method including introducing the DNA directly into the host genome to cause transcription and translation of the genetic information can be mentioned. In this case, it is preferable to join a suitable promoter to the upstream on the 5'-side of the DNA in the host, and it is more preferable to join the terminator to the downstream on the 3'-side. Such promoter and terminator are not particularly limited as long as they are known to function in the cell utilized as the host. For example, the vector, promoter and terminator described in detail in "Basic Course of Microbiology 8 genetic engineering, Kyoritsu Shuppan" can be used.

The host microorganism to be transformed to express the hydrolase of the present invention is not particularly limited as long as the host does not give an adverse influence on dialkyl 2-vinylcyclopropane-1,1-dicarboxylic acid or (1S,2S)-1-alkoxycarbonyl-2-vinylcyclopropane carboxylic acid. For example, the following microorganisms can be mentioned.

Bacteria with established host vector system belonging to the genera *Escherichia, Bacillus, Pseudomonas, Serratia, Brevibacterium, Corynebacterium, Streptococcus, Lactobacillus* and the like.

Actinomycetes with established host vector system belonging to the genera *Rhodococcus, Streptomyces* and the like.

Yeast with established host vector system belonging to the genera *Saccharomyces, Kluyveromyces, Schizosaccharomyces, Zygosaccharomyces, Yarrowia, Trichosporon, Rhodosporidium, Hansenula, Pichia, Candida* and the like.

Molds with established host vector system belonging to the genera *Neurospora, Aspergillus, Cephalosporium, Trichoderma* and the like.

The procedure for preparing the transformant, the construction of the recombinant vector suitable for the host, and the method for culturing the host can be performed according to the techniques conventionally used in the fields of molecular biology, biotechnology, and genetic engineering (e.g., the method described in Molecular Cloning).

Specific examples of a preferred host microorganism, a preferred transformation method in each microorganism, vector, promoter, terminator, and the like are recited in the following; however, the present invention is not limited to these examples.

In *Escherichia*, particularly *Escherichia coli*, the plasmid vector includes, for example, pBR, pUC series plasmids and the like, and promoters derived from lac (β-galactosidase), trp (tryptophan operon), tac, trc (fusion of lac, trp), λ phage PL, PR and the like, and the like. The terminator includes, for example, terminators derived from trpA, derived from phage, derived from rrnB ribosomal RNA and the like.

In *Bacillus*, the vector includes, for example, pUB110 series plasmids, pC194 series plasmids and the like, which may also be integrated with the chromosome. As the promoter and terminator, promoters and terminators of enzyme gene such as alkaline protease, neutral protease, α-amylase and the like, and the like can be utilized.

In *Pseudomonas*, the vector includes, for example, general host vector systems established in *Pseudomonas putida, Pseudomonas cepacia* and the like, a plasmid relating to the decomposition of a toluene compound, broad host range vector based on TOL plasmid (including gene necessary for autonomous replication derived from RSF1010 and the like) pKT240 (Gene, 26, 273-82 (1983)) and the like.

In *Brevibacterium*, particularly *Brevibacterium lactofermentum*, the vector includes, for example, plasmid vectors such as pAJ43 (Gene 39, 281 (1985)) and the like. As the promoter and terminator, various promoters and terminators used in *Escherichia coli* can be used.

In *Corynebacterium*, particularly *Corynebacterium glutamicum*, the vector includes, for example, plasmid vectors such as pCS11 (JP-A-57-183799), pCB101 (Mol. Gen. Genet. 196, 175 (1984)) and the like.

In *Saccharomyces*, particularly *Saccharomyces cerevisiae*, the vector includes, for example, YRp series, YEp series, YCp series, YIp series plasmid and the like. In addition, promoters and terminators of various enzyme genes such as alcohol dehydrogenase, glyceraldehyde-3-phosphate dehydrogenase, acidic phosphatase, β-galactosidase, phosphoglycerate kinase, enolase can be used.

In *Schizosaccharomyces*, the vector includes, for example, plasmid vectors derived from *Schizosaccharomyces pombe* described in Mol. Cell. Biol. 6, 80 (1986) and the like. Particularly, pAUR224 is commercially available from Takara Bio Inc. and can be utilized with ease.

In *Aspergillus, Aspergillus niger, Aspergillus oryzae* and the like are most studied well among molds, integrations into plasmids and chromosomes are available, and promoters derived from extracellular proteases and amylase can be used (Trends in Biotechnology 7, 283-287 (1989)).

In addition to the above, host vector systems corresponding to various microorganisms have been established, and they can be used as appropriate.

In addition to microorganisms, various host/vector systems have been established in plants and animals. Particularly, a system for expressing a large amount of heterologous protein in animals such as insect (e.g., silkworm) and the like (Nature 315, 592-594 (1985)), plants such as *Brassica*, corn, potato and the like, and a system using *Escherichia coli* cell-free extract and a cell-free protein synthesis system of wheat germ and the like has been established, and they can be preferably utilized.

Examples of the treated product of a microorganism or cell having an ability to produce the hydrolase of the present invention include preparations such as the microorganism or cell treated with an organic solvent such as acetone, dimethyl sulfoxide (DMSO), toluene or the like, or a surfactant, or freeze-dry treated, or physically or enzymatically disrupted, or the like, an enzyme fraction in the microorganism or cell which was obtained as a crude product or purified product, and further, those immobilized on a carrier represented by polyacrylamide gel, carageenan gel or the like, and the like.

Examples of the culture solution containing the enzyme obtained by culturing a microorganism or cell having the ability to produce the hydrolase of the present invention include a suspension of the cell and a liquid medium and, when the cell is a type with secretory expression, a supernatant obtained by removing the cell by centrifugation or the like or a concentrate thereof.

2. Composition of the Present Invention

The composition (enzymatic agent) of the present invention contains the hydrolase of the present invention, a microorganism or cell having an ability to produce the enzyme, a treated product of the microorganism or cell, and/or a culture solution containing the enzyme obtained by culturing the microorganism or cell, and catalyzes a reaction to produce (1S,2S)-1-alkoxycarbonyl-2-vinylcyclopropane carboxylic acid by using dialkyl 2-vinylcyclopropane-1,1-dicarboxylic acid as a substrate. Using the composition of the present invention as a catalyst, optically highly pure (1S,2S)-1-alkoxycarbonyl-2-vinylcyclopropane carboxylic acid can be industrially produced with high efficiency at low costs, and the composition is useful.

The composition of the present invention may contain excipient, buffering agent, suspension, stabilizer, preservative, antiseptic, saline and the like in addition to the active ingredient (enzyme, etc.). As the excipient, lactose, sorbitol, D-mannitol, sucrose and the like can be used. As the buffering agent, phosphate, citrate, acetate and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, p-hydroxybenzoic acid, chlorobutanol and the like can be used.

3. Production of Carboxylic Acid Monoester Represented by the Following Formula (II') by Using the Hydrolase of the Present Invention According to the present invention, production shown by the formula (2), namely, a production method of a carboxylic acid monoester represented by the following formula (II'), including reacting the hydrolase of the present invention with a dicarboxylic acid ester represented by the following formula (I') to produce a carboxylic acid monoester represented by the following formula (II'), is provided.

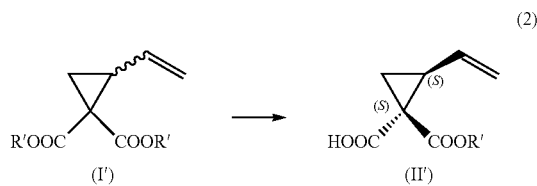

(2)

wherein R' is an optionally substituted alkyl group having 1-10 carbon atoms, an aralkyl group having 7-20 carbon atoms, or an aryl group having 6-12 carbon atoms.

In the formula (2), the "alkyl group with 1-10" of the "optionally substituted alkyl group having 1-10 carbon atoms" for R' is, for example, a linear or branched or cyclic alkyl group having 1-10 carbon atoms, more preferably a linear or branched or cyclic alkyl group having 1-6 carbon atoms. Of these, for example, a methyl group, an ethyl group, an isopropyl group, a normal propyl group, a normal butyl group, an isobutyl group, a sec-butyl group, a tert-butyl group, a normal pentyl group, an isopentyl group, a tert-pentyl group, a neopentyl group, a normal hexyl group, a cyclopropyl group, a cyclobutyl group, a cyclopentyl group, a cyclohexyl group and the like are preferable, an alkyl group having 1-4 carbon atoms is more preferable, a linear or branched alkyl group having 1-4 carbon atoms is further preferable, and an ethyl group is particularly preferable. The substituent of the "optionally substituted alkyl group having 1-10 carbon atoms" is, for example, a halogen atom (e.g., chlorine atom, bromine atom), a linear or branched alkoxy group having 1-6 carbon atoms (e.g., methoxy, ethoxy), a nitro group or the like.

The "aralkyl group having 7-20 carbon atoms" of the "optionally substituted aralkyl group having 7-20 carbon atoms" for R' is, for example, preferably an aralkyl group having 7-12 carbon atoms. Of these, a benzyl group, a 2-phenylethyl group, a 1-phenylethyl group, a 3-phenylpropyl group and the like can be mentioned. The substituent of the "optionally substituted aralkyl group having 7-20 carbon atoms" is, for example, a halogen atom (e.g., chlorine atom, bromine atom), a linear or branched alkyl group having 1-6 carbon atoms (e.g., methyl, ethyl), a linear or branched alkoxy group having 1-6 carbon atoms (e.g., methoxy, ethoxy) or the like. The substituent of the "optionally substituted aralkyl group having 7-20 carbon atoms" is, for example, preferably a benzyl group, a 4-methylbenzyl group, a 4-methoxybenzyl group, a 4-chlorobenzyl group, a 4-bromobenzyl group, a 2-phenylethyl group, a 1-phenylethyl group, a 3-phenylpropyl group or the like.

The "aryl group having 6-12 carbon atoms" of the "optionally substituted aryl group having 6-12 carbon atoms" for R' is, for example, a phenyl group, a 1-naphthyl group, a 2-naphthyl group or the like. The substituent of the "optionally substituted aryl group having 6-12 carbon atoms" is, for example, a halogen atom (e.g., chlorine atom, bromine atom), a linear or branched alkyl group having 1-6 carbon atoms (e.g., methyl, ethyl), a linear or branched alkoxy group having 1-6 carbon atoms (e.g., methoxy, ethoxy), a nitro group or the like. Preferable examples of the "optionally substituted aryl group having 6-12 carbon atoms" include phenyl group, 1-naphthyl group, 2-naphthyl group, o-methylphenyl group, m-methylphenyl group, p-methylphenyl group, o-methoxyphenyl group, m-methoxyphenyl group, p-methoxyphenyl group, 2,3-dimethylphenyl group, 2,4-dimethylphenyl group, 2,5-dimethylphenyl group, 2,6-dimethylphenyl group, 3,4-dimethylphenyl group, 3,5-dimethylphenyl group, 2,3,5-trimethylphenyl group, 2,3,6-trimethylphenyl group, 2,4,6-trimethylphenyl group, o-nitrophenyl group, m-nitrophenyl group, p-nitrophenyl group and the like.

R' is particularly preferably a methyl group, an ethyl group, a tert-butyl group, or a benzyl group, more preferably an ethyl group.

The two R' in the formula (I') may be the same or different, and are preferably the same.

When the hydrolase of the present invention is contacted with a dicarboxylic acid diester represented by the formula (I'), the purified or crudely purified hydrolase of the present invention, a microorganism or cell having an ability to produce the hydrolase of the present invention (e.g., transformant having DNA encoding the polypeptide of the present invention, etc.), a treated product of the microorganism or cell, and/or a culture solution containing the enzyme obtained by culturing the microorganism or cell are/is contacted with the dicarboxylic acid diester represented by the formula (I'), whereby the carboxylic acid monoester represented by the formula (II') can be produced.

The hydrolase of the present invention may be directly used for the reaction. Use of a microorganism or cell having an ability to produce the enzyme, a treated product of the microorganism or cell, and/or a culture solution containing the enzyme obtained by culturing the microorganism or cell is preferable. Among these, use of a transformant having DNA encoding the polypeptide of the present invention is preferable.

As the amount of the microorganism or cell to be added to the reaction mixture, a treated product of the microorganism or cell, and/or a culture solution containing the enzyme obtained by culturing the microorganism or cell is added such that the concentration of the microorganism or cell in the reaction mixture is generally about 0.1 w/v %-50 w/v %, preferably 1 w/v %-20 w/v %, in wet body weight when a microorganism or cell has been added. When a treated product and a culture solution are used, the specific activity of the enzyme is determined, and they are added to achieve the above-mentioned cell concentration. As used herein, w/v % means weight/volume %.

As the dicarboxylic acid diester represented by the formula (I') which is a reaction substrate of the hydrolase of the present invention, (2S) isomer or racemate is generally used.

The reaction method is not particularly limited, and a dicarboxylic acid diester represented by the formula (I') to be the substrate is added to a liquid containing the hydrolase of the present invention, and they are reacted at a suitable temperature and a suitable pressure (e.g., about atmospheric pressure). In this way, a carboxylic acid monoester represented by the formula (II') can be produced.

A dicarboxylic acid diester to be a reaction substrate and represented by the formula (1') is generally used at a substrate concentration of 0.01 w/v %-90 w/v %, preferably 0.1 w/v %-30 w/v. A reaction substrate may be added at once at the start of the reaction. When the enzyme is inhibited by the substrate, the enzyme is desirably added continuously or intermittently to reduce the influence thereof or improve accumulation concentration of the resultant product.

The reaction is generally performed in an aqueous medium or a mixture of the aqueous medium and an organic solvent. Examples of the aqueous medium include water and buffer. As the organic solvent, one showing high solubility of the dicarboxylic acid diester represented by the formula (I') which is the reaction substrate, such as methanol, ethanol, 1-propanol, 2-propanol, 1-butanol, tert-butanol, acetone, dimethyl sulfoxide and the like can be used. As the organic solvent, ethyl acetate, butyl acetate, toluene, chloroform, n-hexane and the like which are effective for removing reaction by-products and the like can also be used.

The reaction is generally performed at a reaction temperature of 4° C.-60° C., preferably 10° C.-45° C., generally under the conditions of pH 3-11, preferably pH 5-8. The reaction time is generally about 1 hr-72 hr.

After completion of the reaction, the carboxylic acid monoester represented by the formula (II') which is produced by the production method of the present invention can be separated by a separation or purification method known to those of ordinary skill in the art, such as centrifugation, membrane treatment, or the like of fungus/bacterium, protein and the like in the reaction mixture after which purified by appropriately combining extraction with organic solvents such as 1-butanol, tert-butanol and the like, distillation, column chromatography using ion exchange resin, silica gel, etc., crystallization at the isoelectric point, crystallization with monohydrochloride, dihydrochloride, calcium salt, etc., and the like.

The hydrolase of the present invention can be particularly preferably used for a method for producing (1S,2S)-1-ethoxycarbonyl-2-vinylcyclopropane carboxylic acid by hydrolyzing diethyl 2-vinylcyclopropane-1,1-dicarboxylic acid.

The dicarboxylic acid diester represented by the formula (I') as a substrate can be produced by the following reaction of the formula (3).

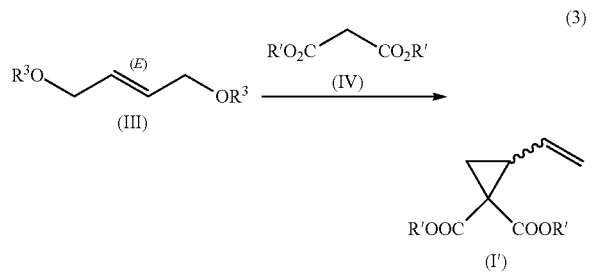

(3)

wherein $R^3$ is an optionally substituted arylsulfonyl group having 6-12 carbon atoms, an optionally substituted alkylsulfonyl group having 1-10 carbon atoms, or an optionally substituted aralkylsulfonyl group having 7-20 carbon atoms, and R' is as defined above.

That is, it can be produced by reacting a compound represented by the formula (III) with a malonic acid ester represented by the formula (IV) in the presence of alkali metal alkoxide or alkali metal hydride.

Examples of the "arylsulfonyl group having 6-12 carbon atoms" of the "optionally substituted arylsulfonyl group having 6-12 carbon atoms" for $R^3$ in the formula (III) include benzenesulfonyl group, 1-naphthalenesulfonyl group, 2-naphthalenesulfonyl group and the like. Examples of the "alkylsulfonyl group having 1-10 carbon atoms" of the "optionally substituted alkylsulfonyl group having 1-10 carbon atoms" include methanesulfonyl group, ethanesulfonyl group, propanesulfonyl group and the like. Examples of the "aralkylsulfonyl group having 7-20 carbon atoms" of the "optionally substituted aralkylsulfonyl group having 7-20 carbon atoms" include benzylsulfonyl group and the like. The substituent of the "optionally substituted arylsulfonyl group having 6-12 carbon atoms", the "optionally substituted alkylsulfonyl group having 1-10 carbon atoms" and the "optionally substituted aralkylsulfonyl group having 7-20 carbon atoms" is, for example, a halogen atom (e.g., chlorine atom, bromine atom), linear or branched alkyl group having 1-6 carbon atoms (e.g., methyl, ethyl), linear or branched alkoxy group having 1-6 carbon atoms (e.g., methoxy, ethoxy), nitro group or the like. Specific preferable examples of $R^3$ include benzenesulfonyl group, p-toluenesulfonyl group, 1-naphthalenesulfonyl group, 2-naphthalenesulfonyl group, methanesulfonyl group, ethanesulfonyl group, propanesulfonyl group, trifluoromethanesulfonyl group, and benzylsulfonyl group and the like. $R^3$ is preferably a methanesulfonyl group, a benzenesulfonyl group or a p-toluenesulfonyl group, particularly preferably a p-toluenesulfonyl group.

A compound represented by the formula (III) which is a starting compound of the formula (3) can be produced according to a known method, for example, the method described in Frederic Dolle et al., Bioorg. Med. Chem. 2006, 14, 1115-1125 or the like. It can also be produced by the following reaction of the formula (4).

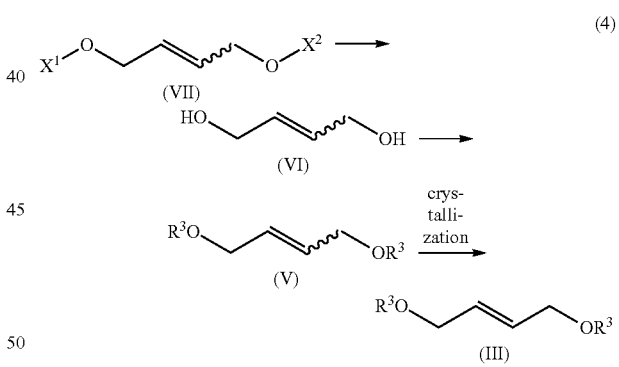

(4)

That is, it can be produced by reacting 1,4-butenediol (VI) with $R^3X$ (X is a halogen atom such as a chlorine atom, a bromine atom, an iodine atom or the like), and crystallizing the obtained compound of the formula (V), or hydrolyzing commercially available starting compound (VII) with an acid or base to give 1,4-butenediol, reacting same with $R^3X$, and crystallizing the obtained compound of the formula (V).

In the formula (4), $X^1$ is a hydrogen atom or $R^1$, $X^2$ is a hydrogen atom or $R^2$, $R^1$ and $R^2$ are each independently an alkylcarbonyl group having 2-11 carbon atoms, an aralkylcarbonyl group having 8-21 carbon atoms, or an arylcarbonyl group having 7-13 carbon atoms, provided that $X^1$ and $X^2$ are not simultaneously hydrogen atoms. Preferably, $X^1$ is $R^1$, and $X^2$ is $R^2$, more preferably $R^1$ and $R^2$ are both acetyl groups, ethylcarbonyl groups, tert-butylcarbonyl groups, or benzoyl groups, further preferably acetyl groups, since they are commercially available as products on the market.

Using the carboxylic acid monoester represented by the formula (II') obtained in the present invention, (1R,2S)-1-amino-1-ethoxycarbonyl-2-vinylcyclopropane (VIII) and a salt thereof which are useful intermediates for the production of various HCV NS3 protease inhibitors and the like under development as therapeutic agents for hepatitis C can be produced. Furthermore, by producing using the thus-obtained carboxylic acid monoester represented by the formula (II'), optically highly pure (1R,2S)-1-amino-1-alkoxy-carbonyl-2-vinylcyclopropane can also be produced with high efficiency at low costs.

(VIII)

While the present invention is explained in further detail in the following by referring to Examples, the present invention is not limited thereto.

EXAMPLE

Example 1: Cloning of Hydrolase Gene

*Rhodococcus* sp. D32 strain was obtained by exploring soil samples using hydrolytic activity as an index. A new hydrolase RsD32Est (SEQ ID NO: 2) was obtained from the analysis of the hydrolase produced by this microorganism and the analysis of gene information. Based on this amino acid sequence information, a codon-optimized gene sequence (SEQ ID NO: 1) for *Escherichia coli* expression encoding RsD32Est was artificially synthesized by DNA2.0 Inc. to obtain pJ411RsD32Est.

Codon-optimized gene sequences (pedst_Ecodon, SEQ ID NO: 3, mcest_Ecodon, SEQ ID NO: 5 and afx20780_Ecodon) for *Escherichia coli* expression that encode *Pseudonocardia dioxanivorans* CB1190 strain, *Microbacterium* chocolatum-derived putative hydrolase PdEst (GenBank Accession No. WP 01367363, SEQ ID NO: 4), McEst (GenBank Accession No. WP 053548180, SEQ ID NO: 6) and hydrolase AFX20780 (GenBank Accession No. AFX20780, SEQ ID NO: 8) were artificially synthesized by DNA2.0 Inc. and inserted into pJExpress411 (manufactured by DNA2.0 Inc.) to produce plasmids (pJ411PdEst, pJ411 McEst and pJ411AFX20780, respectively). The amino acid sequences encoded by the gene sequences were named as RsD32Est, PdEst, McEst, AFX20780, respectively. Respective amino acid sequences are shown in SEQ ID NO: 2 (RsD32Est), SEQ ID NO: 4 (PdEst), SEQ ID NO: 6 (McEst), and SEQ ID NO: 8 (AFX20780).

Using each of the obtained plasmids, *Escherichia coli* BL21 (DE3) (manufactured by Invitrogen Corp.) was transformed according to a conventional method, and recombinant *Escherichia coli* BL21(DE3)/pJ411RsD32Est, BL21 (DE3)/pJ411PdEst, BL21(DE3)/pJ411 McEst and BL21 (DE3)/pJ411AFX20780 were obtained. To obtain bacteria expressing the introduced gene, each recombinant *Escherichia coli* was cultured at 30° C. using a liquid LB medium containing kanamycin and a lac promoter inducer, and the bacteria were harvested after the culture for about 20 hr.

*Escherichia coli* clone No. 26 prepared in Reference Example 1 described later was also cultured at 30° C. using a liquid LB medium containing kanamycin and a lac promoter inducer, and harvested after the culture for about 20 hr.

Example 2

Using each of the bacteria obtained in Example 1, reaction was performed in 100 mmol/L potassium phosphate buffer containing 30 g/L of racemic diethyl 2-vinylcyclopropane-1,1-dicarboxylic acid (hereinafter to be referred to as VCPDE) and 5% dimethyl sulfoxide at a condition of 30° C., pH 7 for 21 hr. As each bacterium, the bacterium obtained by centrifugation from 0.4 mL of the culture solution prepared in Example 1 was used. VCPDE was synthesized according to the method described in the Synthesis Example of JP-B-5657560.

The reaction solution after the reaction for 20 hr was diluted with acetonitrile to an appropriate concentration and analyzed by high performance liquid chromatography (HPLC) under the following conditions. Analysis conditions (1) are analysis conditions for evaluating optical purity. Analysis conditions (2) are analysis conditions for quantifying the Anti isomer containing the (1S,2S) isomer of the produced 1-ethoxycarbonyl-2-vinylcyclopropanecarboxylic acid as the main component and evaluating the production rate of Syn isomer relative to Anti isomer.

Analysis Conditions (1)

column: CHIRALPAK AD-3 (4.6×250 mm, manufactured by Daicel chemical)

eluent:hexane:ethanol:trifluoroacetic acid=95:5:0.1 flow rate: 0.8 ml/min temperature: 30° C.

detection: UV 210 nm

Analysis Conditions (2)

column: COSMOSIL 5C18-MS-II (4.6×250 mm, manufactured by Nacalai Tesque)

eluent A: 0.1% trifluoroacetophenone-containing aqueous solution eluent B: 0.1% trifluoroacetophenone-containing acetonitrile flow rate: 0.8 ml/min temperature: 40° C.

detection: UV 210 nm

TABLE 1

| Gradient program | | |
|---|---|---|
| min | eluent A (%) | eluent B (%) |
| 0 | 75 | 25 |
| 20 | 30 | 70 |
| 23 | 30 | 70 |
| 30 | 75 | 25 |

Table 1 shows the amount of Anti isomer of 1-ethoxycarbonyl-2-vinylcyclopropane carboxylic acid produced using each bacterium, ratio of Syn isomer to Anti isomer in the product, and optical purity.

TABLE 2

| amino acid sequence | Anti isomer (g/L) | ratio of Syn isomer to Anti isomer in the product (%) | optical purity (% e.e.) |
|---|---|---|---|
| RsD32Est | 13.6 | not detected | 99.1 |
| PdEst | 4.28 | not detected | 80.9 |
| McEst | 4.71 | 0.2 | 64.4 |
| AFX20780 | 2.71 | 0.5 | −45.9 |
| PnbA3027-m26 | 2.69 | 14.2 | 99.0 |

As is clear from Table 2, the hydrolase of the present invention having the amino acid sequences shown in SEQ ID NO: 2 (RsD32Est), SEQ ID NO: 4 (PdEst) and SEQ ID NO: 6 (McEst) produces a higher amount of Anti isomer of 1-ethoxycarbonyl-2-vinylcyclopropane carboxylic acid than the conventional hydrolase having the amino acid sequences shown in SEQ ID NO: 8 (AFX20780) and SEQ ID NO: 24 (PnbA3027-m26), and shows low production rate of Syn isomer relative to Anti isomer.

Particularly, the hydrolase of the present invention having the SEQ ID NO: 2 (RsD32Est) produces an extremely high amount of Anti isomer of 1-ethoxycarbonyl-2-vinylcyclopropane carboxylic acid, does not produce Syn isomer, and shows extremely high optical purity.

Figure 2:
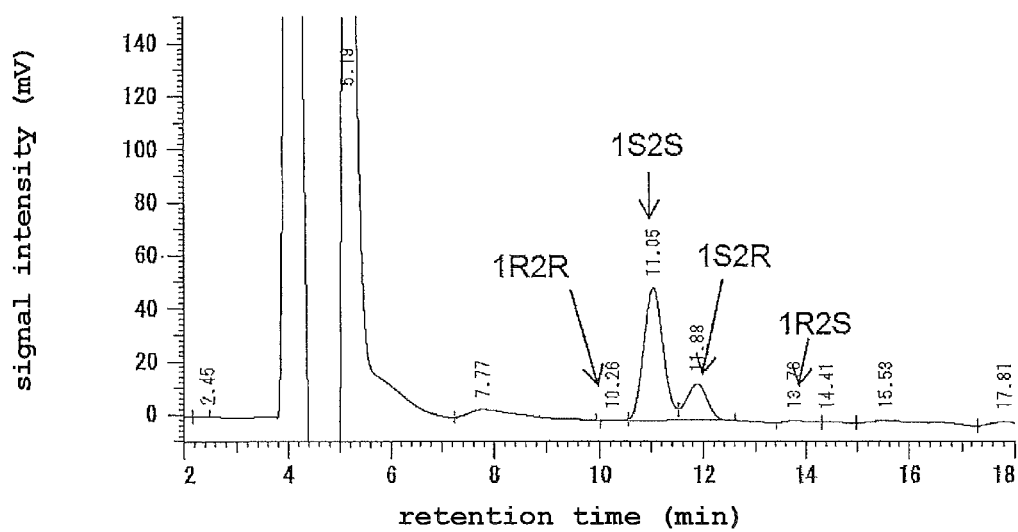
FIG. 2 shows HPLC analysis results of the reaction product obtained using a bacterium having the amino acid sequence PnbA3027-m26.

FIG. 1 shows HPLC analysis results of the reaction product obtained using a bacterium having the amino acid sequence RsD32Est, and FIG. 2 shows HPLC analysis results of the reaction product obtained using a bacterium having the amino acid sequence PnbA3027-m26. As is clear from FIG. 1, the hydrolase of the present invention having the amino acid sequence RsD32Est scarcely produces (1S, 2R) isomer, (1R,2S) isomer or (1R,2R) isomer of 1-ethoxycarbonyl-2-vinylcyclopropane carboxylic acid, and can produce (1S,2S) isomer with high selectivity. As is clear from FIG. 2, conventional hydrolase having the amino acid sequence PnbA3027-m26 shows high production of (1S,2R) isomer of 1-ethoxycarbonyl-2-vinylcyclopropane carboxylic acid, and low selectivity as compared to the hydrolase of the present invention.

Example 3: Production of (1S,2S)-1-ethoxycarbonyl-2-vinylcyclopropane carboxylic acid 1 mol/L potassium phosphate buffer (pH 7.0) (160 mL), desalting water (1332 mL), diethyl 2-vinylcyclopropane-1,1-dicarboxylic acid (84.2 g) and wet bacteria (24 g) of *Escherichia coli* clone BL21(DE3)/pJ411RsD32Est obtained in Example 1 were mixed in a 5 L jar fermentor, and reaction was performed for 24 hr under a sufficient stirring speed at a reaction temperature 30° C. and pH 7.0 during the reaction. The concentration of (1S,2S)-1-ethoxycarbonyl-2-vinylcyclopropane carboxylic acid at the reaction end-point was 22.3 g/L.

Bacteria and bacterial debris were removed from the reaction solution (1100 mL) (pure content of (1S,2S)-1-ethoxycarbonyl-2-vinylcyclopropane carboxylic acid was 22.2 g) after completion of the reaction, toluene (500 mL) was added, and the mixture was stirred at room temperature for 20 min. The toluene layer was separated and the remaining diethyl 2-vinylcyclopropane-1,1-dicarboxylic acid was removed. The pH of the obtained aqueous layer was adjusted to 2.0 by adding 6 N(=3 mol/L) sulfuric acid. Thereafter, toluene (250 mL) was added, and the mixture was stirred at room temperature for 20 min, and a toluene layer containing (1S,2S)-1-ethoxycarbonyl-2-vinylcyclopropane carboxylic acid was obtained. To the obtained aqueous layer was added again toluene (250 mL), and the mixture was stirred at room temperature for 20 min and a toluene layer containing (1S,2S)-1-ethoxycarbonyl-2-vinylcyclopropane carboxylic acid was obtained. As a result of the purity analysis and optical purity analysis of the obtained toluene layer by HPLC analysis, the pure content of (1S,2S)-1-ethoxycarbonyl-2-vinylcyclopropane carboxylic acid was 19.3 g and the optical purity was 99.7% e.e.

Reference Example 1: Cloning of Paranitrobenzyl Esterase Gene (pnbA3027; SEQ ID NO: 9)

Gene Cloning

Chromosome DNA was prepared from the bacteria obtained by culturing *Bacillus subtilis* NBRC3027 overnight in a liquid medium designated by the strain storage organization and using the DNeasy Blood & Tissue Kit (manufactured by QIAGEN).

Primers to amplify the full length of the paranitrobenzyl esterase gene were designed and synthesized based on the gene sequence (pnbA23857, SEQ ID NO: 11) encoding paranitrobenzyl esterase (PNBE23857, GenBank Accession No. AQR87688, SEQ ID NO: 12) derived from *Bacillus subtilis* strain ATCC23857 of known genomic sequences. Respective base sequences are shown in SEQ ID NOs: 13 (pnbA F) and 14 (pnbA R) in the Sequence Listing.

Using the prepared chromosomal DNA as a template, and pnbA F, pnbA R as primers, about 1.5 kbp DNA fragment was amplified by PCR.

Preparation of Expression Vector

Using plasmid pKV32 prepared according to the method described in JP-A-2005-34025 as a template, and the primer (pKVXmaIFW) shown in SEQ ID NO: 15 and the primer (pKVXmaIRV) shown in SEQ ID NO: 16, about 4 kbp fragment was amplified by PCR. The amplified fragment was digested with XmaI, self-closed with the Ligation-Convenience Kit (manufactured by NIPPON GENE Co. Ltd.), and the resulting plasmid was named pKW32.

Preparation of Expression Plasmid

The DNA fragment obtained by the aforementioned gene cloning was introduced according to a conventional method into the cloning vector pKW32 prepared in the aforementioned "Preparation of expression vector". In the following, the obtained plasmid is indicated as ppnbA3027.

The DNA sequence inserted into the plasmid was analyzed and confirmed to contain a gene consisting of 1467 bp ORF. The obtained gene was named pnbA3027 and the sequence is shown in SEQ ID NO: 9. The amino acid sequence encoded by this DNA sequence was named PNBE3027, and the amino acid sequence thereof is shown in SEQ ID NO: 10. The amino acid sequence of PNBE3027 showed 90% sequence identity to the sequence of known PNBE23857.

Reference Example 2: Alteration of Paranitrobenzyl Esterase Gene by Mutation Introduction Using plasmid ppnbA3027 obtained in Reference Example 1 as a template, and the primer (L70FW) shown in SEQ ID NO: 17 and the primer (L70RV) shown in SEQ ID NO: 18 in the Sequence Listing, a random mutation was introduced into the bases encoding leucine at amino acid number 70 by QuikChange Multi Site-Directed Mutagenesis Kit (manufactured by Stratagene Corp.). Similarly, using the primer (L313FW) shown in SEQ ID NO: 19 and the primer (L313RV) shown in SEQ ID NO: 20 in the Sequence Listing, a random mutation was introduced into the bases encoding leucine residue at amino acid number 313. In addition, using the primer (L270 L273FW) shown in SEQ ID NO: 21 and the primer (L270 L273RV) shown in SEQ ID NO: 22 in the Sequence Listing, a random mutation was introduced into the bases encoding leucine residues at amino acid numbers 270 and 273. Using the obtained mutation-introduced plasmid, *Escherichia coli* JM109 (manufactured by Takara Bio Inc.) was transformed according to a conventional method.

Clone No. 26 was isolated from the obtained recombinant *Escherichia coli*, and the DNA sequence inserted into the plasmid possessed by this clone was analyzed. As a result, the sequence thereof (named pnbA3027-26) was as shown in SEQ ID NO: 23. The amino acid sequence encoded by this DNA sequence was named PNBE3027-m26, and the amino acid sequence thereof is shown in SEQ ID NO: 24.

INDUSTRIAL APPLICABILITY

Using the hydrolase of the present invention and the like, optically highly pure (1S,2S)-1-alkoxycarbonyl-2-vinylcyclopropane carboxylic acid can be industrially produced with high efficiency at low costs.

The present invention is based on patent application No. 2018-070188 filed in Japan, the contents of which are encompassed in full herein.

The invention claimed is:

1. A hydrolase consisting of a variant of the amino acid sequence shown in SEQ ID NO: 2 with at least 5 and up to 50 amino acid substitutions, deletions, insertions, and/or additions.

2. A nucleic acid encoding the hydrolase according to claim 1.

3. The nucleic acid according to claim 2, wherein the aforementioned nucleic acid comprises a base sequence of the base sequence shown in SEQ ID NO: 1, with at least 15 and up to 150 nucleotide substitutions, deletions, insertions and/or additions.

4. A method for producing (1S,2S)-1-alkoxycarbonyl-2-vinylcyclopropane carboxylic acid, comprising bringing a hydrolase, a microorganism or cell having an ability to produce the hydrolase, and/or a culture solution containing the hydrolase into contact with dialkyl 2-vinylcyclopropane-1,1-dicarboxylic acid, wherein the hydrolase comprises a polypeptide of the following (a), (b), (c), or (d):
(a) a polypeptide consisting of the amino acid sequence shown in SEQ ID NO: 2;
(b) a polypeptide having an amino acid sequence resulting from the deletion, insertion, substitution, and/or addition of one to 5 amino acids in the amino acid sequence shown in SEQ ID NO: 2, and an activity to catalyze the reaction shown in the formula (1)

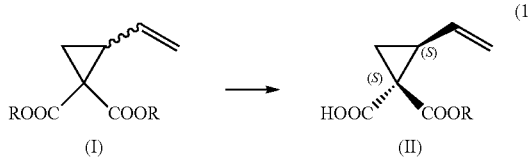

wherein R is an alkyl group having 1-6 carbon atoms in the formula (1), and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%;
(c) a polypeptide consisting of an amino acid sequence with not less than 95% of sequence identity with the amino acid sequence shown in SEQ ID NO: 2, and an activity to catalyze the reaction shown in the abovementioned formula (1), wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%;
(d) a polypeptide consisting of an amino acid sequence with not less than 90% of sequence identity with the amino acid sequence shown in SEQ ID NO: 2, wherein the aforementioned amino acid sequence comprises
(i) 5 consecutive residues DATRG corresponding to residues 75-79 of SEQ ID NO: 2;
(ii) 4 consecutive residues PYGF corresponding to residues 133-136 of SEQ ID NO: 2;
(iii) 4 consecutive residues NWPG corresponding to residues 224-227 of SEQ ID NO: 2; and/or
(iv) 5 consecutive residues PGWPG corresponding to residues 287-291 of SEQ ID NO: 2, and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%.

5. The production method according to claim 4, wherein R in the formula (1) is an ethyl group.

6. A recombinant vector comprising the nucleic acid according to claim 2.

7. A transformant comprising the recombinant vector according to claim 6.

8. The production method according to claim 4, wherein the microorganism or cell is a microorganism or cell transformed with a nucleic acid comprising a base sequence of the following (e), (f), (g), or (h):
(e) the base sequence shown in SEQ ID NO: 1;
(f) a nucleic acid consisting of a base sequence resulting from the substitution, deletion, and/or addition of one to 15 bases in the base sequence shown in SEQ ID NO: 1, and encoding a polypeptide having an activity to catalyze the reaction shown in the formula (1)

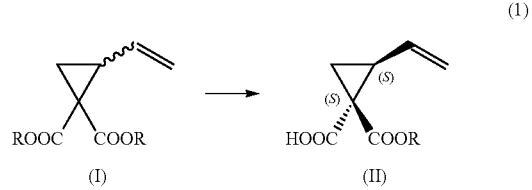

wherein R is an alkyl group having 1-6 carbon atoms in the formula (1), and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%;

(g) a nucleic acid consisting of a base sequence having not less than 98% of sequence identity with the base sequence shown in SEQ ID NO: 1, and encoding a polypeptide having an activity to catalyze the reaction shown in the above-mentioned formula (1);

(h) a nucleic acid having a base sequence that hybridizes with a complementary strand of the base sequence shown in SEQ ID NO: 1 under the condition of washing once at 60° C., 1×SSC, and 0.1% SDS, and encoding a polypeptide having an activity to catalyze the reaction shown in the above-mentioned formula (1), and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%.

9. A recombinant vector comprising the nucleic acid according to claim 3.

10. A method for producing (1S,2S)-1-alkoxycarbonyl-2-vinylcyclopropane carboxylic acid, comprising bringing a treated product of a microorganism or cell having the ability to produce a hydrolase into contact with dialkyl 2-vinylcyclopropane-1,1-dicarboxylic acid, wherein the hydrolase comprises a polypeptide of the following (a), (b), (c), or (d):

(a) a polypeptide consisting of the amino acid sequence shown in SEQ ID NO: 2;

(b) a polypeptide having an amino acid sequence resulting from the deletion, insertion, substitution, and/or addition of one to 5 amino acids in the amino acid sequence shown in SEQ ID NO: 2, and an activity to catalyze the reaction shown in the formula (1)

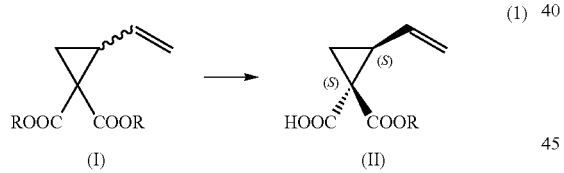

wherein R is an alkyl group having 1-6 carbon atoms in the formula (1), and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%;

(c) a polypeptide consisting of an amino acid sequence with not less than 95% of sequence identity with the amino acid sequence shown in SEQ ID NO: 2, and an activity to catalyze the reaction shown in the above-mentioned formula (1), wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%;

(d) a polypeptide consisting of an amino acid sequence with not less than 90% of sequence identity with the amino acid sequence shown in SEQ ID NO: 2, wherein the aforementioned amino acid sequence comprises:
(i) 5 consecutive residues DATRG corresponding to residues 75-79 of SEQ ID NO: 2;
(ii) 4 consecutive residues PYGF corresponding to residues 133-136 of SEQ ID NO: 2;
(iii) 4 consecutive residues NWPG corresponding to residues 224-227 of SEQ ID NO: 2; and/or
(iv) 5 consecutive residues PGWPG corresponding to residues 287-291 of SEQ ID NO: 2, and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%.

11. The production method according to claim 10, wherein R in the formula (1) is an ethyl group.

12. The production method according to claim 10, wherein the microorganism or cell is a microorganism or cell transformed with a nucleic acid comprising a base sequence of the following (e), (f), (g), or (h):

(e) the base sequence shown in SEQ ID NO: 1;

(f) a nucleic acid consisting of a base sequence resulting from the substitution, deletion, and/or addition of one to 15 bases in the base sequence shown in SEQ ID NO: 1, and encoding a polypeptide having an activity to catalyze the reaction shown in the formula (1)

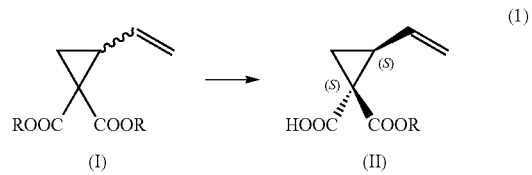

wherein R is an alkyl group having 1-6 carbon atoms in the formula (1), and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%;

(g) a nucleic acid consisting of a base sequence having not less than 98% of sequence identity with the base sequence shown in SEQ ID NO: 1, and encoding a polypeptide having an activity to catalyze the reaction shown in the above-mentioned formula (1);

(h) a nucleic acid having a base sequence that hybridizes with a complementary strand of the base sequence shown in SEQ ID NO: 1, under the condition of washing once at 60° C., 1×SSC, and 0.1% SDS, and encoding a polypeptide having an activity to catalyze the reaction shown in the above-mentioned formula (1), and wherein the production ratio of Syn isomer of the 1-alkoxycarbonyl-2-vinylcyclopropane carboxylic acid in the formula (II) to Anti isomer of the 1-alkoxycarbonyl-2-vinylcyclopropane carboxylic acid is equal to or less than 0.2%.

* * * * *

SEQUENCE LISTING

<160> NUMBER OF SEQ ID NOS: 24

<210> SEQ ID NO 1
<211> LENGTH: 1062
<212> TYPE: DNA
<213> ORGANISM: Artificial Sequence
<220> FEATURE:
<223> OTHER INFORMATION: Ecoli opt

<400> SEQUENCE: 1

```
atgaatctgc caccgggtgt ccgctctgtt acgactcaaa cttcacgtct gcgcttgcat      60
cacttggagg ccggtccggt cgatggcgtg ccactggttc tggtgcacgg taatctgagc     120
tccggtcgtt tctatgaaga tgtgatgccg gccctcgcga aaacctatcg cgtcatcgca     180
ccggatatgc gcggtttcgg tgatagcgag cgcgttaccc tggatgcgac gcgcggtctg     240
gcggactggg cagatgacat tgcggcgctg ctggaagcgt tagacattga ccaggctccg     300
catctgctgg gctggagcac gggtgcaggc gcgattaccc gttacgtcct ggatggtcgt     360
accgccgctt cgctgacgtt gatggacccg gtcccgccgt acggtttcgt cggtatgcac     420
gcagacggca cgccgtggtt tagcgactat gcgggctgtg gtgctggtgt aatgaacacg     480
gaatttaccg agcgtattgc tgctggtgac cgttccaccg attccctggc atctccgcgt     540
aacgttgcgg caggcttttg gggtgaggcg ccgccgatca gccaagagcg tgttgacgtg     600 ctgattacg agctgttgaa aacctgggtt agcgaagata attttccggg tagcgttgtg     660
ccgagcaaaa actggccggg tatcgcccct ggcaccaccg gcatcctgaa cgcactgagc     720
ccgaagtact gcgactggag ccgcatcacc gagctgggta gcaagccgcc gattatgtgg     780
atccagggtg gccaagatga tgtgatcagc aatgcgagcc acaacgaccc ggcgaccctg     840
ggcgcagcgg gcctgatccc gggttggccg ggcgaagatg tctgcccggc gcagccgatg     900
atcacccaga ttcgtgatgt gttgcaagca tacgaagatg ccggcggccg tacgcgtacc     960
gagtggttcg aggcaagcca ccatctgcct atgattgaag aaccggaccg ttggctgcaa    1020
gccgtgtcta gctttgtggc ggaagccgac gcgattgcgt aa                       1062
```

<210> SEQ ID NO 2
<211> LENGTH: 353
<212> TYPE: PRT
<213> ORGANISM: Rhodococcus sp. D32

<400> SEQUENCE: 2

```
Met Asn Leu Pro Pro Gly Val Arg Ser Val Thr Thr Gln Thr Ser Arg
1               5                   10                  15

Leu Arg Leu His His Leu Glu Ala Gly Pro Val Asp Gly Val Pro Leu
            20                  25                  30
```

Val Leu Val His Gly Asn Leu Ser Ser Gly Arg Phe Tyr Glu Asp Val
         35                  40                  45
Met Pro Ala Leu Ala Lys Thr Tyr Arg Val Ile Ala Pro Asp Met Arg
 50                  55                  60
Gly Phe Gly Asp Ser Glu Arg Val Thr Leu Asp Ala Thr Arg Gly Leu
 65                  70                  75                  80
Ala Asp Trp Ala Asp Asp Ile Ala Ala Leu Glu Ala Leu Asp Ile
                 85                  90                  95
Asp Gln Ala Pro His Leu Leu Gly Trp Ser Thr Gly Ala Gly Ala Ile
                100                 105                 110
Thr Arg Tyr Val Leu Asp Gly Arg Thr Ala Ala Ser Leu Thr Leu Met
            115                 120                 125
Asp Pro Val Pro Pro Tyr Gly Phe Val Gly Met His Ala Asp Gly Thr
130                 135                 140
Pro Trp Phe Ser Asp Tyr Ala Gly Cys Gly Ala Gly Val Met Asn Thr
145                 150                 155                 160
Glu Phe Thr Glu Arg Ile Ala Ala Gly Asp Arg Ser Thr Asp Ser Leu
                165                 170                 175
Ala Ser Pro Arg Asn Val Ala Ala Gly Phe Trp Gly Glu Ala Pro Pro
            180                 185                 190
Ile Ser Gln Glu Arg Val Asp Val Leu Ile Asp Glu Leu Leu Lys Thr
        195                 200                 205
Trp Val Ser Glu Asp Asn Phe Pro Gly Ser Val Val Pro Ser Lys Asn
210                 215                 220
Trp Pro Gly Ile Ala Pro Gly Thr Thr Gly Ile Leu Asn Ala Leu Ser
225                 230                 235                 240
Pro Lys Tyr Cys Asp Trp Ser Arg Ile Thr Glu Leu Gly Ser Lys Pro
                245                 250                 255
Pro Ile Met Trp Ile Gln Gly Gly Gln Asp Asp Val Ile Ser Asn Ala
            260                 265                 270
Ser His Asn Asp Pro Ala Thr Leu Gly Ala Ala Gly Leu Ile Pro Gly
        275                 280                 285
Trp Pro Gly Glu Asp Val Cys Pro Ala Gln Pro Met Ile Thr Gln Ile
290                 295                 300
Arg Asp Val Leu Gln Ala Tyr Glu Asp Ala Gly Gly Arg Thr Arg Thr
305                 310                 315                 320
Glu Trp Phe Glu Ala Ser His His Leu Pro Met Ile Glu Glu Pro Asp
                325                 330                 335
Arg Trp Leu Gln Ala Val Ser Ser Phe Val Ala Glu Ala Asp Ala Ile
            340                 345                 350
Ala

<210> SEQ ID NO 3
<211> LENGTH: 1053
<212> TYPE: DNA
<213> ORGANISM: Artificial Sequence
<220> FEATURE:
<223> OTHER INFORMATION: Ecoli opt

<400> SEQUENCE: 3
atgcagctgt tgcctggtgt tcgtagcgtg gtggtcccaa ctgatcgtct ggaagttcat      60
ttggtggagt atggtcctga agagggcgtt ccggttgtga tgctgcacgg taaccttttct    120 accggtcgtt tctttgagca cctgttcccg ggtgccccgc agggttaccg tatcatcgca     180

```
ccggacatgc gttgctttgg cgatacggaa cgtctgccgt tagacgcaac ccgtggcctg      240
gctgactggg ccgatgacgt tgcggctctg ctgcgtgcac tgcgcgttga gcgtccggtt      300
cacctcctgg gctggagcac tgcgggcgcg gccattgtgg attttgcaag cgcgcatccg      360
gtcacctctc tgaccttcct ggatccggtc agcccgtacg gtttcggtgg cgtgctggcg      420
gatggtacgc cgtgcttccc ggactttgcc ggttccggcg gcggcattgt gaatccagaa      480
gtcgtccgtc gcctggccga gggtgacgat acgaccgaga gcccgttttc tattcgcagc      540
gtcatgcgtg gctcgtattg gttggaaagc catagcgaac cgcgcgaaga tctgctggta      600
gcagaagtgc tgaaaaccgt gaccggcgac gacaattatc ctggtgactc cgtcgcgagc      660
ccgaattggc cgggtagcgc accgggtacg accggtatca tcaacgctct gagcccgaag      720
tactgtaact ggacgcgcgt tgttgacctg atccgaaac cgccggtttt gtggacgcat       780
ggtgccgagg acaccgtcgt cgcggatgcg agcatgcaag acctgggtac cctgggcgag      840
ctgggttacg tgccgggctg gccggtgca tgtgttcc cgagccagcc gatggtgagc         900
caaattcgcg aagtcctggg ccgttacgcg gcggcgggtg ccacgttcg caccgagatc       960
ctgccgggtg cgggccactc cccgcacatt gagctgccag aactgtggag cggtgtgttt     1020
tgggacttcg ttggtgcggc ggagcgtggt taa                                  1053

<210> SEQ ID NO 4
<211> LENGTH: 350
<212> TYPE: PRT
<213> ORGANISM: Pseusdonocardia dioxanivorans CB1190

<400> SEQUENCE: 4

Met Gln Leu Leu Pro Gly Val Arg Ser Val Val Pro Thr Asp Arg
1               5                   10                  15

Leu Glu Val His Leu Val Glu Tyr Gly Pro Glu Glu Gly Val Pro Val
                20                  25                  30

Val Met Leu His Gly Asn Leu Ser Thr Gly Arg Phe Phe Glu His Leu
            35                  40                  45

Phe Pro Gly Ala Pro Gln Gly Tyr Arg Ile Ile Ala Pro Asp Met Arg
        50                  55                  60

Cys Phe Gly Asp Thr Glu Arg Leu Pro Leu Asp Ala Thr Arg Gly Leu
65                  70                  75                  80

Ala Asp Trp Ala Asp Asp Val Ala Ala Leu Leu Arg Ala Leu Arg Val
                85                  90                  95

Glu Arg Pro Val His Leu Leu Gly Trp Ser Thr Ala Gly Ala Ala Ile
            100                 105                 110

Val Asp Phe Ala Ser Ala His Pro Val Thr Ser Leu Thr Phe Leu Asp
        115                 120                 125

Pro Val Ser Pro Tyr Gly Phe Gly Gly Val Leu Ala Asp Gly Thr Pro
    130                 135                 140

Cys Phe Pro Asp Phe Ala Gly Ser Gly Gly Ile Val Asn Pro Glu
145                 150                 155                 160

Val Val Arg Arg Leu Ala Glu Gly Asp Asp Thr Thr Glu Ser Pro Phe
                165                 170                 175

Ser Ile Arg Ser Val Met Arg Gly Ser Tyr Trp Leu Glu Ser His Ser
            180                 185                 190

Glu Pro Arg Glu Asp Leu Leu Val Ala Glu Val Leu Lys Thr Val Thr
        195                 200                 205

Gly Asp Asp Asn Tyr Pro Gly Asp Ser Val Ala Ser Pro Asn Trp Pro
    210                 215                 220
```

```
Gly Ser Ala Pro Gly Thr Thr Gly Ile Ile Asn Ala Leu Ser Pro Lys
225                 230                 235                 240

Tyr Cys Asn Trp Thr Arg Val Val Asp Leu Asp Pro Lys Pro Pro Val
                245                 250                 255

Leu Trp Thr His Gly Ala Glu Asp Thr Val Val Ala Asp Ala Ser Met
            260                 265                 270

Gln Asp Leu Gly Thr Leu Gly Glu Leu Gly Tyr Val Pro Gly Trp Pro
        275                 280                 285

Gly Ala Asp Val Phe Pro Ser Gln Pro Met Val Ser Gln Ile Arg Glu
    290                 295                 300

Val Leu Gly Arg Tyr Ala Ala Ala Gly Gly His Val Arg Thr Glu Ile
305                 310                 315                 320

Leu Pro Gly Ala Gly His Ser Pro His Ile Glu Leu Pro Glu Leu Trp
                325                 330                 335

Ser Gly Val Phe Trp Asp Phe Val Gly Ala Ala Glu Arg Gly
            340                 345                 350

<210> SEQ ID NO 5
<211> LENGTH: 1113
<212> TYPE: DNA
<213> ORGANISM: Artificial Sequence
<220> FEATURE:
<223> OTHER INFORMATION: Ecoli opt

<400> SEQUENCE: 5
atgaccctgt tgatggcat cacttcgcgt attgttgaca ccgatcgtct gaccgtgaat      60
attctggagc gtgcggcaga cgatccgcaa acgccgcctg atcgcacggt tgttttgtg    120 catggtaacg tcagcagcgc gctgttttgg caagaaatta tgcaagacct cccgagcgat   180
ctgcgtgcta tcgcggtgga tctgcgtggc ttcggtggca gcgagcacgc accggtcgac   240
gcgacccgtg tgttcgcga tttcagcgat gacttgcacg caacgctgga agcactggat   300
atcccggtcg cacacctggt cggttggagc atgggtggcg gcgtggttat gcagtatgca   360
ttagaccatc cggttttgag cctgacgctg cagtccccgg tcagcccgta cggtttcggt   420
ggcacccgtc gtgacggcag ccgtctgact gatgacgatg ctggctgcgg tggcggcggc   480
gccaatccgg atttcattca gcgtctgatc gaccacgaca cgtccgacga cgcgcagacc   540
agcccgcgct ccgttttccg tgcgggttac gtagcgagcg attacaccac ggaccacgaa   600
gatgtgtggg tggagagcat gctgaccacc tctaccgcgg acggcaatta cccaggtgac   660
gccgtcccga cgacaactg gccaggtttt gccgcgggtc gccacggtgt tctgaacacg   720
atggcgcctc aatacttcga tgtcagcggt atcgttgatc tggcggagaa accgccgatt   780
ttgtggatcc atggtaccgc ggatgcgatt gtgtccgacg cgagctttta tgacctgaac   840
tatctgggtc agctgggtat cgtgccgggt tggccgggtg aagatgtcgc tccggcccaa   900
gaaatggtta gccagacgcg cgacgtcctg ggccgttacg ctgcgggtgg cggcaccgtt   960
accgaagttg ccgttgaggg tgcgggtcac agcgcacatt tggagcgtcc ggccgtgttc  1020
cgccacgcgc tgctggaaat tattggttat gtgggtgcgg ctgctgaccc ggcaccgccg  1080
actgaagcaa tcatcatccg ctctgccgac taa                                1113

<210> SEQ ID NO 6
<211> LENGTH: 370
<212> TYPE: PRT
<213> ORGANISM: Microbacterium chocolatum
```

```
<400> SEQUENCE: 6

Met Thr Leu Phe Asp Gly Ile Thr Ser Arg Ile Val Asp Thr Asp Arg
 1               5                  10                  15

Leu Thr Val Asn Ile Leu Glu Arg Ala Ala Asp Asp Pro Gln Thr Pro
             20                  25                  30

Pro Asp Arg Thr Val Val Phe Val His Gly Asn Val Ser Ala Leu
         35                  40                  45

Phe Trp Gln Glu Ile Met Gln Asp Leu Pro Ser Asp Leu Arg Ala Ile
     50                  55                  60

Ala Val Asp Leu Arg Gly Phe Gly Ser Glu His Ala Pro Val Asp
 65                  70                  75                  80

Ala Thr Arg Gly Val Arg Asp Phe Ser Asp Asp Leu His Ala Thr Leu
             85                  90                  95

Glu Ala Leu Asp Ile Pro Val Ala His Leu Val Gly Trp Ser Met Gly
            100                 105                 110

Gly Gly Val Val Met Gln Tyr Ala Leu Asp His Pro Val Leu Ser Leu
        115                 120                 125

Thr Leu Gln Ser Pro Val Ser Pro Tyr Gly Phe Gly Thr Arg Arg
130                 135                 140

Asp Gly Ser Arg Leu Thr Asp Asp Ala Gly Cys Gly Gly Gly Gly
145                 150                 155                 160

Ala Asn Pro Asp Phe Ile Gln Arg Leu Ile Asp His Asp Thr Ser Asp
            165                 170                 175

Asp Ala Gln Thr Ser Pro Arg Ser Val Phe Arg Ala Gly Tyr Val Ala
        180                 185                 190

Ser Asp Tyr Thr Thr Asp His Glu Asp Val Trp Val Glu Ser Met Leu
    195                 200                 205

Thr Thr Ser Thr Ala Asp Gly Asn Tyr Pro Gly Asp Ala Val Pro Ser
210                 215                 220

Asp Asn Trp Pro Gly Phe Ala Ala Gly Arg His Gly Val Leu Asn Thr
225                 230                 235                 240

Met Ala Pro Gln Tyr Phe Asp Val Ser Gly Ile Val Asp Leu Ala Glu
            245                 250                 255

Lys Pro Pro Ile Leu Trp Ile His Gly Thr Ala Asp Ala Ile Val Ser
        260                 265                 270

Asp Ala Ser Phe Tyr Asp Leu Asn Tyr Leu Gly Gln Leu Gly Ile Val
    275                 280                 285

Pro Gly Trp Pro Gly Glu Asp Val Ala Pro Ala Gln Glu Met Val Ser
290                 295                 300

Gln Thr Arg Asp Val Leu Gly Arg Tyr Ala Ala Gly Gly Gly Thr Val
305                 310                 315                 320

Thr Glu Val Ala Val Glu Gly Ala Gly His Ser Ala His Leu Glu Arg
            325                 330                 335

Pro Ala Val Phe Arg His Ala Leu Leu Glu Ile Ile Gly Tyr Val Gly
        340                 345                 350

Ala Ala Ala Asp Pro Ala Pro Pro Thr Glu Ala Ile Ile Ile Arg Ser
    355                 360                 365

Ala Asp
370

<210> SEQ ID NO 7
<211> LENGTH: 894
<212> TYPE: DNA
<213> ORGANISM: Artificial Sequence
```

<220> FEATURE:
<223> OTHER INFORMATION: Ecoli opt

<400> SEQUENCE: 7

```
atggaaaagc gcagcattac tctgaaaaac ggtgaagttt acaaatacgt ggaacagggt      60
cagggcgacc aagttctgct gctgatccat ggcaacttta gctccagcct gcacttcacc     120
ccgttgctgg agcgcctgcc gaagaacatt aaggttattg cgccggactt gcgtggttat     180
ggtgattcat cttactatcg tcgtatcagc tctctgaacg acttcgcgga agatgtccac     240
atgtttatgg aagccaaaga aattaaaagc taccacgtag ttggctggag cctgggtggc     300
ggcgtggcgc tggaactggc ggcacatcat ccagaggctg tggagtcctt ggtgctcatc     360
aacagcacca cgcacaaggg ttatccggtg ttcaagaaag gtgcggatgg taagccactg     420
gtcggtgaag tctatcaaag cgccgatgag atggcaaatg atccggtcca agtcctgccg     480
ctgctgaagg ctcaaaaaga taagaatttt gactttgtta gctatatctt cgatgttacc     540
atttacaccg tgaataagcc ttcggtggat gacaacaagc tgtggattaa cgaaagcctg     600
aaacagcgta atctgccgga tgcagactgg gcgctggcga atttgaacat gagcgaccag     660
cacaatttct acaatgccgg tatgaacaat atctccaagg ttaaggcacc ggtgctgcac     720
acgtggggcg acaaagatat taccgtgccg gagtatatga tcaaagacaa tgtgaaagcg     780
ctggaagaac aaagcaaact ggtcgtctac gagaactgcg ccatagccc gctggttgat     840
gttccggacc agctgacgaa agacatcctg gactttatcg gttacaaggg ttaa          894
```

<210> SEQ ID NO 8
<211> LENGTH: 297
<212> TYPE: PRT
<213> ORGANISM: Unknown
<220> FEATURE:
<223> OTHER INFORMATION: patented sequence

<400> SEQUENCE: 8

```
Met Glu Lys Arg Ser Ile Thr Leu Lys Asn Gly Glu Val Tyr Lys Tyr
1               5                   10                  15

Val Glu Gln Gly Gln Gly Asp Gln Val Leu Leu Leu Ile His Gly Asn
            20                  25                  30

Phe Ser Ser Ser Leu His Phe Thr Pro Leu Leu Glu Arg Leu Pro Lys
        35                  40                  45

Asn Ile Lys Val Ile Ala Pro Asp Leu Arg Gly Tyr Gly Asp Ser Ser
    50                  55                  60

Tyr Tyr Arg Arg Ile Ser Ser Leu Asn Asp Phe Ala Glu Asp Val His
65                  70                  75                  80

Met Phe Met Glu Ala Lys Glu Ile Lys Ser Tyr His Val Val Gly Trp
                85                  90                  95

Ser Leu Gly Gly Gly Val Ala Leu Glu Leu Ala Ala His His Pro Glu
            100                 105                 110

Ala Val Glu Ser Leu Val Leu Ile Asn Ser Thr Thr His Lys Gly Tyr
        115                 120                 125

Pro Val Phe Lys Lys Gly Ala Asp Gly Lys Pro Leu Val Gly Glu Val
    130                 135                 140

Tyr Gln Ser Ala Asp Glu Met Ala Asn Asp Pro Val Gln Val Leu Pro
145                 150                 155                 160

Leu Leu Lys Ala Gln Lys Asp Lys Asn Phe Asp Phe Val Ser Tyr Ile
                165                 170                 175

Phe Asp Val Thr Ile Tyr Thr Val Asn Lys Pro Ser Val Asp Asp Asn
```

```
                180               185               190
Lys Leu Trp Ile Asn Glu Ser Leu Lys Gln Arg Asn Leu Pro Asp Ala
            195                 200                 205

Asp Trp Ala Leu Ala Asn Leu Asn Met Ser Asp Gln His Asn Phe Tyr
        210                 215                 220

Asn Ala Gly Met Asn Asn Ile Ser Lys Val Lys Ala Pro Val Leu His
225                 230                 235                 240

Thr Trp Gly Asp Lys Asp Ile Thr Val Pro Glu Tyr Met Ile Lys Asp
                245                 250                 255

Asn Val Lys Ala Leu Glu Glu Gln Ser Lys Leu Val Val Tyr Glu Asn
            260                 265                 270

Cys Gly His Ser Pro Leu Val Asp Val Pro Asp Gln Leu Thr Lys Asp
        275                 280                 285

Ile Leu Asp Phe Ile Gly Tyr Lys Gly
        290                 295

<210> SEQ ID NO 9
<211> LENGTH: 1470
<212> TYPE: DNA
<213> ORGANISM: Bacillus subtilis NBRC3027

<400> SEQUENCE: 9
atgactcatc aaatagtaac gactcaatac ggcaaagtaa aaggcacaac agaaaatggc      60
gtacataaat ggaaaggcat cccctatgcc agaccgcctg tcgggccatt gcgttttaaa     120
gcaccggaac ctccggaagc gtgggagaac gaactggacg caacagcgta cggccctatt     180
tgcccgcagc cgtctgattt gctgtcactt tcgtataatg agctgccccg ccagtctgag     240
aattgcttgt atgtcaatgt atttgcgcct gatactccaa gtcaaaacct gcctgtcatg     300
gtgtggattc acggcggcgc tttttatctt ggagcgggca gtgagccatt attcgatggg     360
tcaagacttg cggcgcaggg agaagtcatt gtcgttacac tgaattatcg actggggccg     420
tttggatttt tacatttgtc ttcgtttgat gaggcgtatt ccgataaccct tggtcttttg     480
gaccaagccg ccgcactgaa atgggtgcga gacaatatct cagcatttgg cggtgatccg     540
gataacgtaa cggtatttgg agaatccgct ggcggcatga gcattgccgc gctgctcgca     600
atgcctgcgg caaaaggcct gttccagaaa gcgatcatgg aaagcggcgc ttctagaaca     660
atgacaacag aaaaagcggc tagcactgca gcagcctttt tacaggtcct tgggattaac     720
gagagccaat ggacagact gcacactgta tctgcggaag atttgcttaa agcggccgat     780
aagcttcgga aagcagaaaa tgaaaatctc tttcagctgt tattccagcc cgcccttgat     840
ccgaaaacgc tgcctgctga accagaaaaa gcaatcgcag gaggtgctgc tgccgacatt     900
ccgctgttaa tcggaacaaa ccgcgatgaa ggatatttat ttttcacccc ggactcagac     960
gttcattctc aagaaacgtt taatgccgcg cttgagtatt tattggaaca gccgctggca    1020
aagaaagccg ccgatctgta tccgcgttca ctagaaagcc aaattcatat gatgactgat    1080
ttgttatttt ggcgcccggc cgtcgcctat gcctccgctc agtctcaata cgcgcctgta    1140
tggatgtacc gatttgattg gcactctgat aagccgccat acaataaggc gtttcacgca    1200
ttagagcttc cttttgtttt cggaaatctg gacgggttag aacgaatggc aaaagcagag    1260
gttacggatg aggtgaaacg gctttctcat accatacaat cagcatggat cacgtttgcc    1320
aaaacaggaa acccaagcac cgaagatgta aaatggccgg cgtatcatga agaaacaaga    1380
cagacgctga ttttagattc agagattacg atcgaaaacg atcctgaatc tgaaaaaagg    1440
```
cagaagctat tcccttcaaa aggagaataa                                1470

<210> SEQ ID NO 10
<211> LENGTH: 489
<212> TYPE: PRT
<213> ORGANISM: Bacillus subtilis NBRC3027

<400> SEQUENCE: 10

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Arg Pro
            20                  25                  30

Pro Val Gly Pro Leu Arg Phe Lys Ala Pro Glu Pro Glu Ala Trp
        35                  40                  45

Glu Asn Glu Leu Asp Ala Thr Ala Tyr Gly Pro Ile Cys Pro Gln Pro
    50                  55                  60

Ser Asp Leu Leu Ser Leu Ser Tyr Asn Glu Leu Pro Arg Gln Ser Glu
65                  70                  75                  80

Asn Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Phe Asp Gly Ser Arg Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Asp Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Thr Glu
    210                 215                 220

Lys Ala Ala Ser Thr Ala Ala Ala Phe Leu Gln Val Leu Gly Ile Asn
225                 230                 235                 240

Glu Ser Gln Leu Asp Arg Leu His Thr Val Ser Ala Glu Asp Leu Leu
                245                 250                 255

Lys Ala Ala Asp Lys Leu Arg Lys Ala Glu Asn Glu Asn Leu Phe Gln
            260                 265                 270

Leu Leu Phe Gln Pro Ala Leu Asp Pro Lys Thr Leu Pro Ala Glu Pro
        275                 280                 285

Glu Lys Ala Ile Ala Gly Gly Ala Ala Ala Asp Ile Pro Leu Leu Ile
    290                 295                 300

Gly Thr Asn Arg Asp Glu Gly Tyr Leu Phe Phe Thr Pro Asp Ser Asp
305                 310                 315                 320

Val His Ser Gln Glu Thr Phe Asn Ala Ala Leu Glu Tyr Leu Leu Glu
                325                 330                 335

Gln Pro Leu Ala Lys Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365
```

```
Ala Tyr Ala Ser Ala Gln Ser Gln Tyr Ala Pro Val Trp Met Tyr Arg
        370                 375                 380

Phe Asp Trp His Ser Asp Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Val Thr Asp Glu Val Lys Arg Leu Ser His Thr Ile
                420                 425                 430

Gln Ser Ala Trp Ile Thr Phe Ala Lys Thr Gly Asn Pro Ser Thr Glu
                435                 440                 445

Asp Val Lys Trp Pro Ala Tyr His Glu Glu Thr Arg Gln Thr Leu Ile
450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 11
<211> LENGTH: 1470
<212> TYPE: DNA
<213> ORGANISM: Bacillus subtilis ATCC23857

<400> SEQUENCE: 11
atgactcatc aaatagtaac gactcaatac ggcaaagtaa aaggcacaac ggaaaacggc      60
gtacataagt ggaaaggcat ccctatgcc aagccgcctg tcggacaatg cgttttaaa      120 gcacctgagc cgcctgaagt gtgggaagat gtgcttgatg ccacagcgta cggctctatt     180
tgcccgcagc cgtctgattt gctgtcactt tcgtatactg agctgccccg ccagtccgag     240
gattgcttgt atgtcaatgt atttgcgcct gacaccccaa gtaaaaatct tcctgtcatg     300
gtgtggattc acggaggcgc tttttatcta ggagcgggca gtgagccatt gtatgacgga     360
tcaaaacttg cggcacaggg agaagtcatt gtcgttacat gaactatcg gctgggccg      420 tttggctttt tgcacttgtc ttcatttaat gaggcgtatt ctgataacct tgggctttta     480
gaccaagccg ccgcgctgaa atgggtgcga gagaatattt cagcgtttgg cggtgatccc     540
gataacgtaa cagtatttgg agaatccgcc ggcgggatga gcattgccgc gctgcttgct     600
atgcctgcgg caaaaggcct gttccagaaa gcaatcatgg aaagcggcgc ttctcgaacg     660
atgacgaaag aacaagcggc gagcacctcg gcagcctttt tacaggtcct tgggattaac     720
gagggccaac tggataaaat tgcatacggtt tctgcggaag attttgctaaa agcggctgat    780 cagcttcgga ttgcagaaaa agaaaaatatc tttcagctgt tcttccagcc cgccttgat     840 ccgaaaacgc tgcctgaaga accagaaaaa gcgatcgcag aaggggctgc ttccggtatt     900
ccgctattaa ttggaacaac ccgtgatgaa ggatatttat ttttcacccc ggattcagac     960
gttcattctc aggaaacgct tgatgcagcg ctcgagtatt tactagggaa gccgctggca    1020
gagaaagttg ccgatttgta tccgcgttct ctggaaagcc aaattcatat gatgactgat    1080
ttattatttt ggcgccctgc cgtcgcctat gcatccgcac agtctcatta cgcccctgtc    1140
tggatgtaca ggttcgattg gcacccgaag aagccgccgt acaataaagc gtttcacgca    1200
ttagagcttc cttttgtctt tggaaatctg gacggattgg aacgaatggc aaaagcggag    1260
attacggatg aggtgaaaca gctttctcac acgatacaat cagcgtggat cacgttcgcc    1320
aaaacaggaa acccaagcac cgaagctgtg aattggcctg cgtatcatga gaaaacgaga    1380
gagacgctga ttttagactc agagattacg atcgaaaacg atcccgaatc tgaaaaaagg    1440
```
cagaagctat tcccttcaaa aggagaataa                                      1470

<210> SEQ ID NO 12
<211> LENGTH: 489
<212> TYPE: PRT
<213> ORGANISM: Bacillus subtilis ATCC23857

<400> SEQUENCE: 12

Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Lys Pro
            20                  25                  30

Pro Val Gly Gln Trp Arg Phe Lys Ala Pro Glu Pro Pro Glu Val Trp
        35                  40                  45

Glu Asp Val Leu Asp Ala Thr Ala Tyr Gly Ser Ile Cys Pro Gln Pro
    50                  55                  60

Ser Asp Leu Leu Ser Leu Ser Tyr Thr Glu Leu Pro Arg Gln Ser Glu
65                  70                  75                  80

Asp Cys Leu Tyr Val Asn Val Phe Ala Pro Asp Thr Pro Ser Lys Asn
                85                  90                  95

Leu Pro Val Met Val Trp Ile His Gly Gly Ala Phe Tyr Leu Gly Ala
            100                 105                 110

Gly Ser Glu Pro Leu Tyr Asp Gly Ser Lys Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asn Glu Ala Tyr Ser Asp Asn Leu Gly Leu Leu
145                 150                 155                 160

Asp Gln Ala Ala Ala Leu Lys Trp Val Arg Glu Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Lys Glu
    210                 215                 220

Gln Ala Ala Ser Thr Ser Ala Ala Phe Leu Gln Val Leu Gly Ile Asn
225                 230                 235                 240

Glu Gly Gln Leu Asp Lys Leu His Thr Val Ser Ala Glu Asp Leu Leu
                245                 250                 255

Lys Ala Ala Asp Gln Leu Arg Ile Ala Glu Lys Glu Asn Ile Phe Gln
            260                 265                 270

Leu Phe Phe Gln Pro Ala Leu Asp Pro Lys Thr Leu Pro Glu Glu Pro
        275                 280                 285

Glu Lys Ala Ile Ala Glu Gly Ala Ala Ser Gly Ile Pro Leu Leu Ile
    290                 295                 300

Gly Thr Thr Arg Asp Glu Gly Tyr Leu Phe Phe Thr Pro Asp Ser Asp
305                 310                 315                 320

Val His Ser Gln Glu Thr Leu Asp Ala Ala Leu Glu Tyr Leu Leu Gly
                325                 330                 335

Lys Pro Leu Ala Glu Lys Val Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

-continued

```
Ala Tyr Ala Ser Ala Gln Ser His Tyr Ala Pro Val Trp Met Tyr Arg
        370                 375                 380

Phe Asp Trp His Pro Lys Lys Pro Pro Tyr Asn Lys Ala Phe His Ala
385                 390                 395                 400

Leu Glu Leu Pro Phe Val Phe Gly Asn Leu Asp Gly Leu Glu Arg Met
                405                 410                 415

Ala Lys Ala Glu Ile Thr Asp Glu Val Lys Gln Leu Ser His Thr Ile
            420                 425                 430

Gln Ser Ala Trp Ile Thr Phe Ala Lys Thr Gly Asn Pro Ser Thr Glu
        435                 440                 445

Ala Val Asn Trp Pro Ala Tyr His Glu Glu Thr Arg Glu Thr Leu Ile
    450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
gcgaattcat gactcatcaa atagtaacga ctc                               33

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
gctctagatt attctccttt tgaagggaat agc                               33

<210> SEQ ID NO 15
<211> LENGTH: 32
<212> TYPE: DNA
<213> ORGANISM: Artificial Sequence
<220> FEATURE:
<223> OTHER INFORMATION: primer

<400> SEQUENCE: 15
tccccccggg tcaaggcgca ctcccgttct gg                                32

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
tccccccggg tggggtgcct aatgagtgag ctaac                             35

<210> SEQ ID NO 17
<211> LENGTH: 40
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 17
ccgtctgatt tgctgtcann ktcgtataat gagctgcccc                          40

<210> SEQ ID NO 18
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(22)
<223> OTHER INFORMATION: n is a, c, g, or t

<400> SEQUENCE: 18
ggggcagctc attatacgam nntgacagca aatcagacgg                          40

<210> SEQ ID NO 19
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(18)
<223> OTHER INFORMATION: n is a, c, g, or t

<400> SEQUENCE: 19
ccgcgatgaa ggatatnnkt ttttcacccc gg                                  32

<210> SEQ ID NO 20
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(16)
<223> OTHER INFORMATION: n is a, c, g, or t

<400> SEQUENCE: 20
ccggggtgaa aaamnnatat ccttcatcgc gg                                  32

<210> SEQ ID NO 21
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 21
gcttcggaaa gcagaaaatg aaaatnnktt tcagnnktta ttccagcccg ccc           53
```

<210> SEQ ID NO 22
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 22
gggcgggctg gaataamnnc tgaaamnnat tttcattttc tgctttccga agc       53

<210> SEQ ID NO 23
<211> LENGTH: 1470
<212> TYPE: DNA
<213> ORGANISM: Bacillus subtilis NBRC3027

<400> SEQUENCE: 23
atgactcatc aaatagtaac gactcaatac ggcaaagtaa aaggcacaac agaaaatggc      60
gtacataaat ggaaaggcat cccctatgcc agaccgcctg tcgggccatt gcgttttaaa     120
gcaccggagc ctccggaagc gtgggagaac gaactggacg caacagcgta cggcccatt     180 tgcccgcagc cgtctgattt gctgtcagat tcgtataatg agctgccccg ccagtctgag     240
aattgcttgt atgtcaatgt atttgcgcct gatactccaa gtcaaaacct gcctgtcatg     300
gtgtggattc acggcggcgc ttttatctt ggagcgggca gtgagccatt attcgatggg     360
tcaagacttg cggcgcaggg agaagtcatt gtcgttacac tgaattatcg actggggccg     420
tttggatttt tacatttgtc ttcgtttgat gaggcgtatt ccgataaccct tggtcttttg     480 gaccaagccg ccgcactgaa atgggtgcga gacaatatct cagcatttgg cggtgatccg     540
gataacgtaa cggtatttgg agaatccgct ggcggcatga gcattgccgc gctgctcgca     600
atgcctgcgg caaaaggcct gttccagaaa gcgatcatgg aaagcggcgc ttctagaaca     660
atgacaacag aaaaagcggc tagcactgca gcagccttt tacaggtcct tgggattaac     720
gagagccaat tggacagact gcacactgta tctgcggaag atttgcttaa agcggccgat     780
aagcttcgga aagcagaaaa tgaaaatcag tttcagcggt tattccagcc cgcccttgat     840
ccgaaaacgc tgcctgctga accagaaaaa gcaatcgcag gaggtgctgc tgccgacatt     900
ccgctgttaa tcggaacaaa ccgcgatgaa ggatatatgt ttttcacccc ggactcagac     960
gttcattctc aagaaacgtt taatgccgcg cttgagtatt tattggaaca gccgctggca    1020
aagaaagccg ccgatctgta tccgcgttca ctagaaagcc aaattcatat gatgactgat    1080
ttgttatttt ggcgcccggc cgtcgcctat gcctccgctc agtctcaata cgcgcctgta    1140
tggatgtacc gatttgattg gcactctgat aagccgccat acaataaggc gtttcacgca    1200
ttagagcttc ctttttgtttt cggaaatctg gacgggttag aacgaatggc aaaagcagag    1260
gttacggatg aggtgaaacg gctttctcat accatacaat cagcatggat cacgtttgcc    1320
aaaacaggaa acccaagcac cgaagatgta aaatggccgg cgtatcatga agaaacaaga    1380
cagacgctga ttttagattc agagattacg atcgaaaacg atcctgaatc tgaaaaaagg    1440
cagaagctat tcccttcaaa aggagaataa                                     1470

<210> SEQ ID NO 24

<211> LENGTH: 489
<212> TYPE: PRT
<213> ORGANISM: Bacillus subtilis NBRC3027

<400> SEQUENCE: 24

```
Met Thr His Gln Ile Val Thr Thr Gln Tyr Gly Lys Val Lys Gly Thr
1               5                   10                  15

Thr Glu Asn Gly Val His Lys Trp Lys Gly Ile Pro Tyr Ala Arg Pro
            20                  25                  30

Pro Val Gly Pro Leu Arg Phe Lys Ala Pro Glu Pro Glu Ala Trp
        35                  40                  45

Glu Asn Glu Leu Asp Ala Thr Ala Tyr Gly Pro Ile Cys Pro Gln Pro
    50                  55                  60

Ser Asp Leu Leu Ser Asp Ser Tyr Asn Glu Leu Pro Arg Gln Ser Glu
65                  70                  75                  80

Asn Cys Leu Tyr Val Asn Val Phe Ala Pro Asp Thr Pro Ser Gln Asn
                85                  90                  95

Leu Pro Val Met Val Trp Ile His Gly Gly Ala Phe Tyr Leu Gly Ala
            100                 105                 110

Gly Ser Glu Pro Leu Phe Asp Gly Ser Arg Leu Ala Ala Gln Gly Glu
        115                 120                 125

Val Ile Val Val Thr Leu Asn Tyr Arg Leu Gly Pro Phe Gly Phe Leu
    130                 135                 140

His Leu Ser Ser Phe Asp Glu Ala Tyr Ser Asp Asn Leu Gly Leu Leu
145                 150                 155                 160

Asp Gln Ala Ala Ala Leu Lys Trp Val Arg Asp Asn Ile Ser Ala Phe
                165                 170                 175

Gly Gly Asp Pro Asp Asn Val Thr Val Phe Gly Glu Ser Ala Gly Gly
            180                 185                 190

Met Ser Ile Ala Ala Leu Leu Ala Met Pro Ala Ala Lys Gly Leu Phe
        195                 200                 205

Gln Lys Ala Ile Met Glu Ser Gly Ala Ser Arg Thr Met Thr Thr Glu
    210                 215                 220

Lys Ala Ala Ser Thr Ala Ala Ala Phe Leu Gln Val Leu Gly Ile Asn
225                 230                 235                 240

Glu Ser Gln Leu Asp Arg Leu His Thr Val Ser Ala Glu Asp Leu Leu
                245                 250                 255

Lys Ala Ala Asp Lys Leu Arg Lys Ala Glu Asn Glu Asn Gln Phe Gln
            260                 265                 270

Arg Leu Phe Gln Pro Ala Leu Asp Pro Lys Thr Leu Pro Ala Glu Pro
        275                 280                 285

Glu Lys Ala Ile Ala Gly Gly Ala Ala Ala Asp Ile Pro Leu Leu Ile
    290                 295                 300

Gly Thr Asn Arg Asp Glu Gly Tyr Met Phe Phe Thr Pro Asp Ser Asp
305                 310                 315                 320

Val His Ser Gln Glu Thr Phe Asn Ala Ala Leu Glu Tyr Leu Leu Glu
                325                 330                 335

Gln Pro Leu Ala Lys Lys Ala Ala Asp Leu Tyr Pro Arg Ser Leu Glu
            340                 345                 350

Ser Gln Ile His Met Met Thr Asp Leu Leu Phe Trp Arg Pro Ala Val
        355                 360                 365

Ala Tyr Ala Ser Ala Gln Ser Gln Tyr Ala Pro Val Trp Met Tyr Arg
    370                 375                 380

Phe Asp Trp His Ser Asp Lys Pro Pro Tyr Asn Lys Ala Phe His Ala
```

```
385                 390                 395                 400
Leu Glu Leu Pro Phe Val Phe Gly Asn Leu Asp Gly Leu Glu Arg Met
                405                 410                 415

Ala Lys Ala Glu Val Thr Asp Glu Val Lys Arg Leu Ser His Thr Ile
                420                 425                 430

Gln Ser Ala Trp Ile Thr Phe Ala Lys Thr Gly Asn Pro Ser Thr Glu
                435                 440                 445

Asp Val Lys Trp Pro Ala Tyr His Glu Glu Thr Arg Gln Thr Leu Ile
            450                 455                 460

Leu Asp Ser Glu Ile Thr Ile Glu Asn Asp Pro Glu Ser Glu Lys Arg
465                 470                 475                 480

Gln Lys Leu Phe Pro Ser Lys Gly Glu
                485
```